(12) United States Patent
Jorissen

(10) Patent No.: US 8,608,676 B2
(45) Date of Patent: Dec. 17, 2013

(54) MOISTURE RESISTANT MOLDABLE INJURY THERAPY DEVICE AND METHOD

(75) Inventor: Koen Jozef Maria Jorissen, Hamburg (DE)

(73) Assignee: BSN Medical, Inc., Charlotte, NC (US)

(*) Notice: Subject to any disclaimer, the term of this patent is extended or adjusted under 35 U.S.C. 154(b) by 0 days.

(21) Appl. No.: 13/478,380

(22) Filed: May 23, 2012

(65) Prior Publication Data

US 2012/0259258 A1  Oct. 11, 2012

Related U.S. Application Data

(63) Continuation-in-part of application No. 12/972,681, filed on Dec. 20, 2010.

(60) Provisional application No. 61/416,066, filed on Nov. 22, 2010.

(51) Int. Cl.
*A61F 5/00* (2006.01)
*A61F 13/00* (2006.01)

(52) U.S. Cl.
USPC .................. 602/5; 602/8; 602/21; 602/64

(58) Field of Classification Search
USPC .......... 602/60–64, 20–22, 5–8; 128/878, 879, 128/882
See application file for complete search history.

(56) References Cited

U.S. PATENT DOCUMENTS

| 4,770,299 | A | * | 9/1988 | Parker .......................... 206/409 |
| 5,520,621 | A | | 5/1996 | Edenbaum et al. |
| 5,755,678 | A | | 5/1998 | Parker et al. |
| 6,146,348 | A | * | 11/2000 | Slautterback ................... 602/21 |
| 6,186,969 | B1 | * | 2/2001 | Bell et al. ......................... 602/64 |
| D477,409 | S | * | 7/2003 | Mills et al. .................... D24/190 |
| 6,730,053 | B1 | * | 5/2004 | Bodenschatz et al. .......... 602/64 |
| 6,835,182 | B2 | * | 12/2004 | Darcey ............................ 602/20 |
| 7,033,331 | B1 | | 4/2006 | Hely |
| 2004/0193083 | A1 | | 9/2004 | Evans et al. |
| 2005/0234374 | A1 | | 10/2005 | Grim et al. |
| 2007/0239093 | A1 | | 10/2007 | Wyatt et al. |

OTHER PUBLICATIONS

International Search Report and Written Opinion for PCT/US10/61521, date Feb 28, 2011.
International Search Report and Written Opinion for PCT/US12/39069, date Sep. 6, 2012.

* cited by examiner

*Primary Examiner* — Kim M Lewis
(74) *Attorney, Agent, or Firm* — Shumaker, Loop & Kendrick, LLP

(57) ABSTRACT

A moisture-resistant multi-phase orthopedic system and method including a single layer, three-dimensional knitted fabric having an open structure for providing enhanced moisture transfer from the skin outwardly into the atmosphere and a flap carried by the body and movable between an open position and a closed position overlying a part of the cast body to be applied to a treatment area of the limb. The flap is adapted to cover and retain between the cast body and the flap the splint worn by the patient during the initial treatment phase in the same position as the location of the splint during the initial treatment phase.

17 Claims, 28 Drawing Sheets

MOISTURE RESISTANT MOLDABLE INJURY THERAPY DEVICE AND METHOD

CROSS-REFERENCE TO RELATED APPLICATIONS

This application is a continuation-in-part application which claims priority to U.S. patent application Ser. No. 12/972,681 filed Dec. 20, 2010, which claims priority of U.S. Provisional Patent Application Ser. No. 61/416,066 filed Nov. 22, 2010, the contents of which are incorporated by reference herein.

TECHNICAL FIELD AND BACKGROUND OF THE INVENTION

This invention relates to orthopedic splint and casting products, and in particular, to an orthopedic system that provides cost-saving, efficient and medically beneficial casting and splinting procedures that are particularly efficient in resisting moisture retention during wear. The invention also relates to a method of treating fractures, limb injuries and the like during multiple treatment phases.

Bone fracture treatment is a multi-phase process that includes management of the fracture in an acute phase, post-acute phase, and a later rehabilitation phase. Conventional treatments use different formats and applications with the materials constructed in different ways to offer support and comfort during the entire treatment process from acute management immediately after the injury to a substantially healed state where support is no longer required at all times.

Splinting immobilizes injured extremities and prevents further injury, decreases pain and bleeding, and allows healing to take place. There are many indications for splinting an extremity, including temporary immobilization for several orthopedic problems other than fractures; including dislocations, injury of muscles, tendons, and ligaments, protection of vascular/nerve repairs, and postsurgical wound protection, all of which under specific circumstances may find aspects of the invention useful.

The present invention provides casting and splinting products that are particularly effective in managing moisture retention during use. This is accomplished by a novel selection and adoption of fibers that cooperate to permit moisture to efficiently migrate away from the skin of the patient through the structure of the product to the atmosphere.

It is another object of the invention to provide a casting and splinting product that eliminates waste by enabling molded splinting materials used during an acute treatment stage to be retained and used during post-acute treatment and rehabilitation to ensure accurate and proper fit of the supporting structure. These procedures will ensure maximum clinical benefits by reducing misalignment and poor fitting of the splint during all phases of treatment.

The current methods of fracture support rely on medical interventions that use a series of casting and splinting regimes at various times during the process of healing and rehabilitation. This conventional methodology can often require the use of a plaster of Paris cast, followed by a synthetic cast followed by a synthetic splint to complete the repair and rehabilitation of the fracture. Each of these steps requires the patient to visit a clinic or hospital to have the existing device removed, and fitted with a new device. In other instances, particularly with severe displaced fractures and attendant severe swelling, a splint is first applied to stabilize the limb until swelling has subsided, then a cast or additional splint is applied.

The present invention involves a new and improved therapy that permits the use of the original cast in an acute phase of immobilization through to stabilization of the injury and physiotherapy.

More specifically, the present invention involves a new and improved approach to repairing a bone fracture, among other conditions, by using the original splint or cast which is fitted/molded to the anatomy for an acute phase of immobilization and then removed and fitted into a soft goods orthopedic brace or cast for further stabilization and rehabilitation of the injury. This process ensures a correctly fitted and molded device that can be used throughout all treatment phases with minimal interference for the patient, optimum use of the materials and device and efficient moisture management.

BRIEF SUMMARY OF THE INVENTION

Therefore, it is an object of the invention to provide a moisture-resistant fracture management system that efficiently manages moisture retention during wear.

It is another object of the invention to provide a moisture-resistant fracture management system that utilizes at least some elements of the treatment device during more than one treatment phase.

It is another object of the invention to provide a moisture-resistant fracture management system that provides improved fit between the affected limb and the fracture management device.

It is another object of the invention to provide a moisture-resistant fracture management system that results in cost-saving, efficient and medically-efficacious casting and splinting procedures.

To achieve the foregoing and other aspects and advantages, in one embodiment a moisture-resistant multi-phase orthopedic system is provided that includes a sleeve formed of moisture-impervious material and sealable to prevent entry of moisture, and a moldable splint positioned in the sleeve and sealed therein against entry of moisture until use. The splint includes a substrate, a reactive system impregnated into or coated onto the substrate that remains stable when maintained in substantially moisture-free conditions and hardens upon exposure to sufficient moisture to form a rigid, self supporting structure. A cover encloses the substrate along its length and forms a barrier between the substrate and a limb during an initial treatment phase during which the splint is worn by a patient on the limb. An elongate removable wrap is provided for retaining the splint on the limb. A removable cast is provided for application to the limb during a subsequent treatment phase, and includes a cast body having an interior side and exterior side formed of a moisture resistant, single layer, three-dimensional double knit fabric having an open structure for providing enhanced moisture transfer from the skin of the patient outwardly into the atmosphere. A flap is carried by the body and movable between an open position and a closed position overlying a part of the cast body to be applied to a treatment area of the limb. The flap is adapted to cover and retain between the cast body and the flap. The splint is worn by the patient during the initial treatment phase in the same position as the location of the splint during the initial treatment phase.

According to one preferred embodiment of the invention, the substrate is pre-formed into a shape suitable for application to a limb to be treated.

According to another preferred embodiment of the invention, the moisture resistant fabric includes a soft, conformable, single layer, three-dimensional double bar knitted fabric providing enhanced moisture transfer from the skin outwardly into the atmosphere, and having a moisture transfer rate (MVTR) of between 500 and 600 g/m²/24 hrs.

According to another preferred embodiment of the invention, the moisture resistant fabric includes a soft, conformable, single layer, three-dimensional double bar knitted fabric providing enhanced moisture transfer from the skin outwardly into the atmosphere, and having a moisture transfer rate (MVTR) of about 560 g/m²/24 hrs.

According to another preferred embodiment of the invention, the cast includes a padding layer positioned on the cast to overlie a part of the cast body to be applied to the treatment area of the limb.

According to another preferred embodiment of the invention, the cast is a short arm cast adapted for being placed on a forearm of a patient, and includes a thumb recess portion positioned for receiving the thumb and a retention strap for retaining the thumb recess portion around the thumb.

According to another preferred embodiment of the invention, a method of immobilizing a limb in multiple treatment phases is provided and includes the steps providing a sleeve formed of moisture-impervious material and sealable to prevent entry of moisture, and a splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb. An elongate removable wrap is provided for retaining the splint on the limb; and a removable cast is provided for application to the limb, and includes a cast body having an interior side and exterior side and formed of a moisture resistant, single layer, three-dimensional double knit fabric having an open structure for enhanced moisture transfer from the skin of the patient outwardly into the atmosphere. A flap is carried by the body and movable between an open position, and a closed position overlying a part of the cast body to be applied to a treatment area of the limb and to cover and retain the splint between the cast body and the flap. The method further includes the steps of removing the splint from the sleeve, wetting the splint, molding the splint to the limb, securing the splint in its molded position to the limb for being worn during an initial orthopedic treatment phase, removing the splint from the limb, placing the splint between the flap and the cast body of the cast, and releasably applying the cast and the splint to the limb for being worn during a subsequent orthopedic treatment phase.

According to another preferred embodiment of the invention, the method includes the step of pre-forming the substrate into a shape suitable for application to a limb to be treated.

According to another preferred embodiment of the invention, the method includes the step of providing an elongate medical bandage material substantially the same length as the sleeve and positioned in the sleeve in a single length along the length of the sleeve, and a seal for resealing the sleeve against entry of moisture after a predetermined length of the bandage material has been dispensed from the sleeve for use to prevent hardening of the substrate of the bandage material remaining in the sleeve.

According to another preferred embodiment of the invention, the invention includes the step of removing the cover from the substrate before placing the splint between the flap and the cast body of the cast.

According to another preferred embodiment of the invention, a moisture-resistant removable cast is provided for application to a limb during an orthopedic treatment phase, and includes a cast body having an interior side and exterior side, and a flap carried by the body and formed of a moisture resistant, single layer, three-dimensional double knit fabric having an open structure for enhanced moisture transfer from the skin of the patient outwardly into the atmosphere and movable between an open position, and a closed position overlying a part of the cast body to be applied to a treatment area of the limb. The flap is adapted to cover and retain between the cast body and the flap a splint worn by a patient during an initial treatment phase.

According to another preferred embodiment of the invention, a padding layer is provided that is positioned on the cast to overlie a part of the cast body to be applied to the treatment area of the limb.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DETAILED DESCRIPTION OF THE PREFERRED EMBODIMENT AND BEST MODE

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

The present invention has application in various types and combinations of fracture treatment methods, phases and devices. For purposes of illustration, this application describes the invention as used in a treatment process wherein a rigid splint is applied and molded to a fractured limb during an acute or post-acute phase of treatment, followed by use of the substrate portion of the splint as a support in a cast during either a post-acute or rehabilitation phase of treatment. It is understood, however, that the various elements of the invention can also be used sequentially with a plaster of Paris or synthetic cast or splint as medically required.

Figure 1:
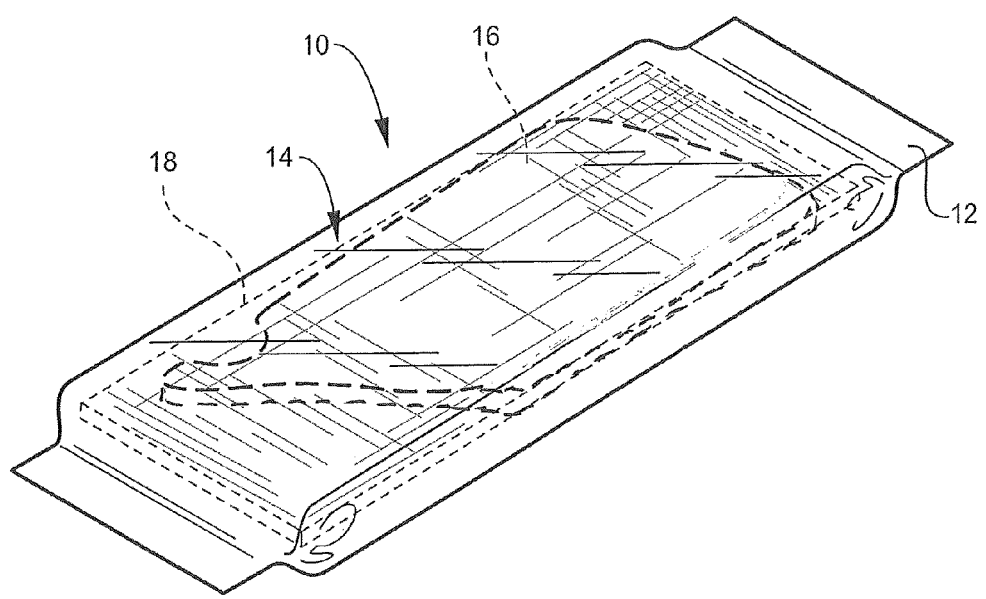
FIG. 1 is a perspective view of a precut form of splint in its storage package.
Figure 2:
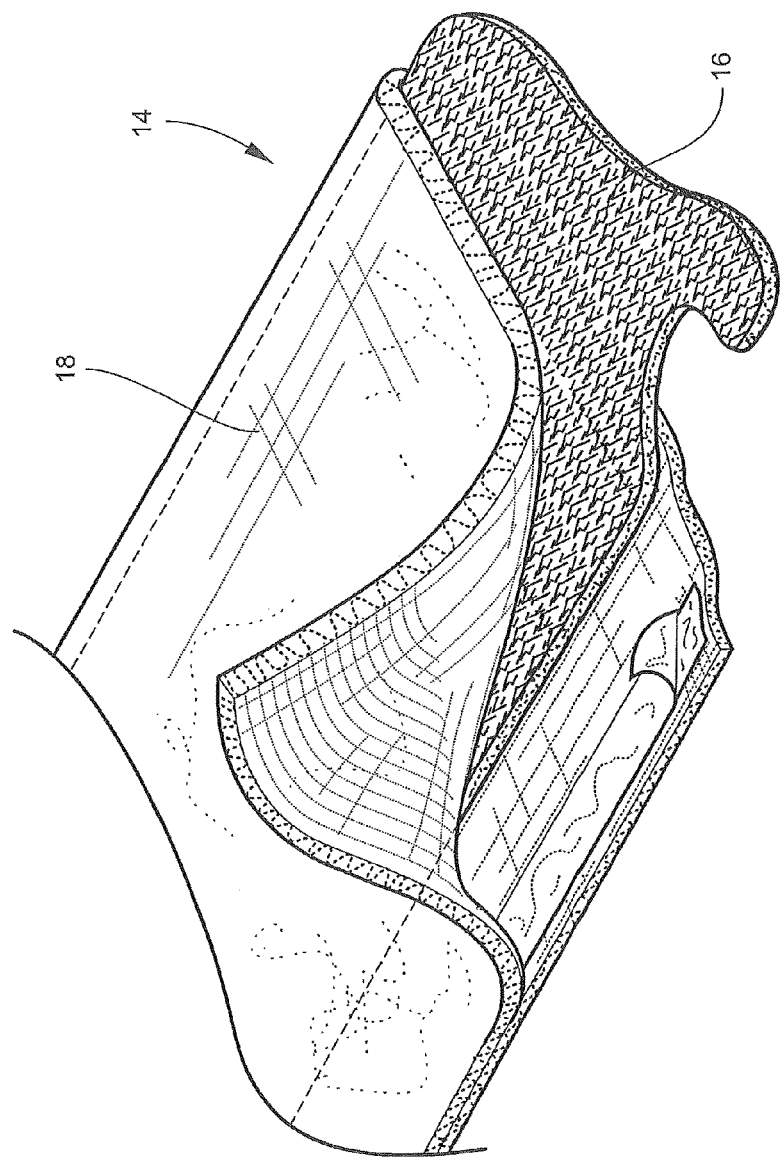
FIG. 2 is a perspective view, with a portion of the cover cut away, showing the substrate portion of the splint.
Figure 3:
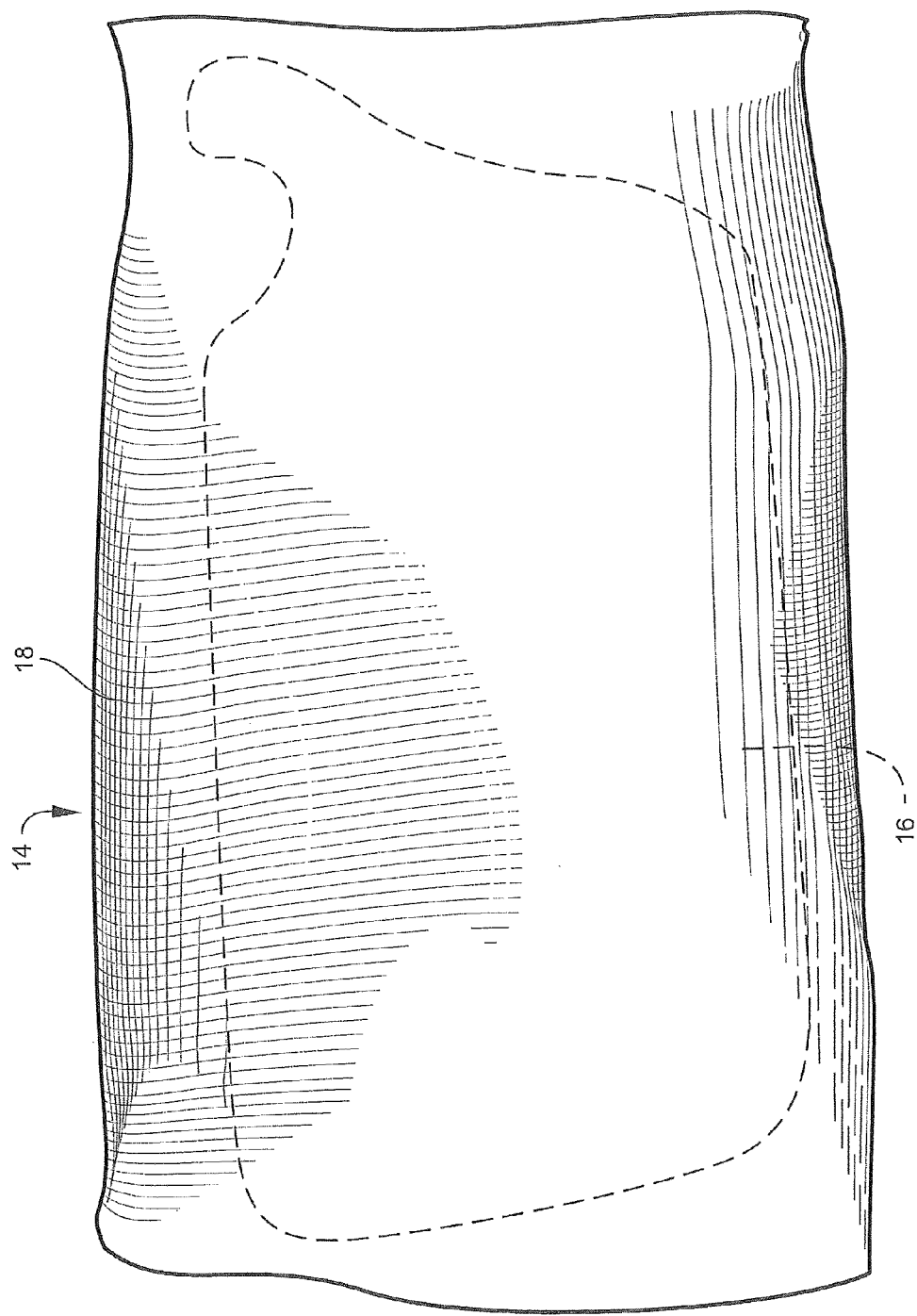
FIG. 3 is a top plan view showing the splint cover enclosing the substrate.

Referring now specifically to the drawings, FIGS. 1-3 illustrate one preferred embodiment of a splint product 10 that includes an outer water and moisture-proof envelope 12, for example, laminated plastic and foil, within which a splint 14 is sealed in moisture-free condition. As best shown in FIGS. 2 and 3, the splint 14 is formed of a substrate of woven, knitted or non-woven fabric substrate 16 enclosed within an outer cover 18.

In a preferred embodiment, the substrate 16 is constructed from a non-glass spacer fabric knitted from a 455 decitex 96 filament high tenacity polyester on 5 of the knitting machine needlebars with a weight of >6.0 grams/denier. Other suitable synthetic fabrics, as well as fiberglass fabric, may also be used. The 6th needlebar is threaded using a 2-fold 167 decitex textured polyester yarn. The 6th bar is the middle needlebar and positions the textured polyester yarn to prevent the hardenable resin from leeching out of the fabric. The substrate 16 preferably weighs 410 grams/m², and is constructed with 32 wales and 32 courses/cm. The substrate 16 is preferably about 3 mm thick.

The substrate 16 is coated or impregnated with a moisture/water activated hardenable resin of known type such as, for example, that disclosed in applicant's U.S. Pat. No. 4,770,299. The moisture/water activated hardenable substrate 16 will become rigid in approximately 15 minutes, with strength of >1.6 kgf/cms. This is sufficiently rigid to stabilize a bone fracture in both animals and humans.

The cover 18 is constructed from a polypropylene monofilament 0.1 mm yarn, and the fabric is knitted on 3 of 4 knitting machine needlebars. The 4th bar is on the outside of the cover 18 and produces a flat polypropylene yarn, 100 denier, 72 filament, to wick the moisture away from the wearer's skin. The monofilament yarn is formed in the center of the cover 18 and acts as a drainage route for water and/or moisture. The fabric will normally dry completely in 90 minutes or less, depending on ambient temperature and humidity. The moisture vapor transmission rate for fabric of the cover 18 is 580 grams/m²/24 hours.

Figure 4:
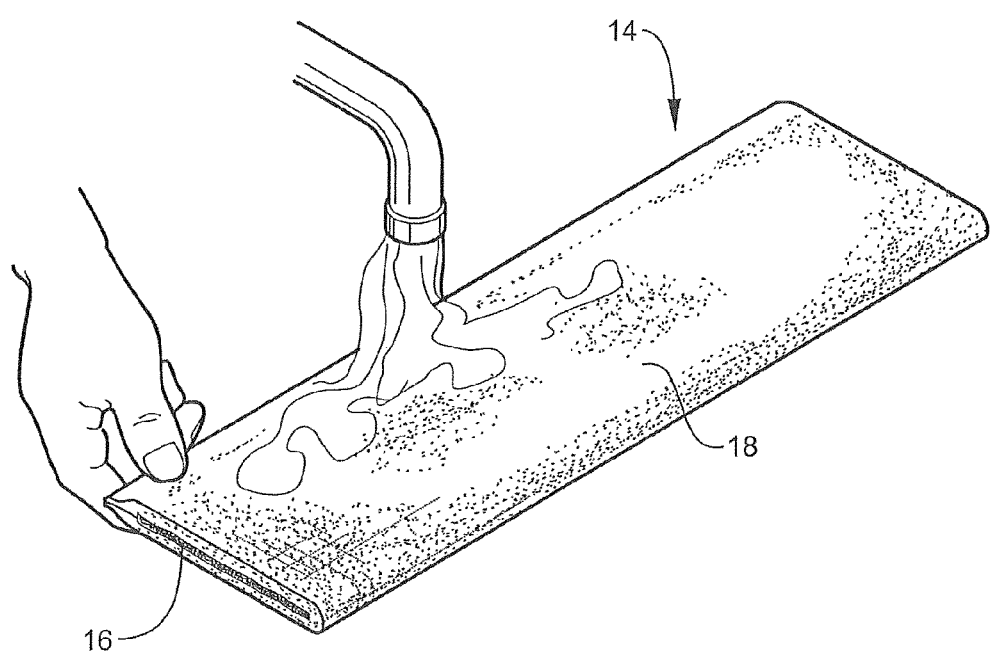
FIG. 4 illustrates wetting of the splint after removal from its storage package prior to application to the fracture site.
Figure 5:
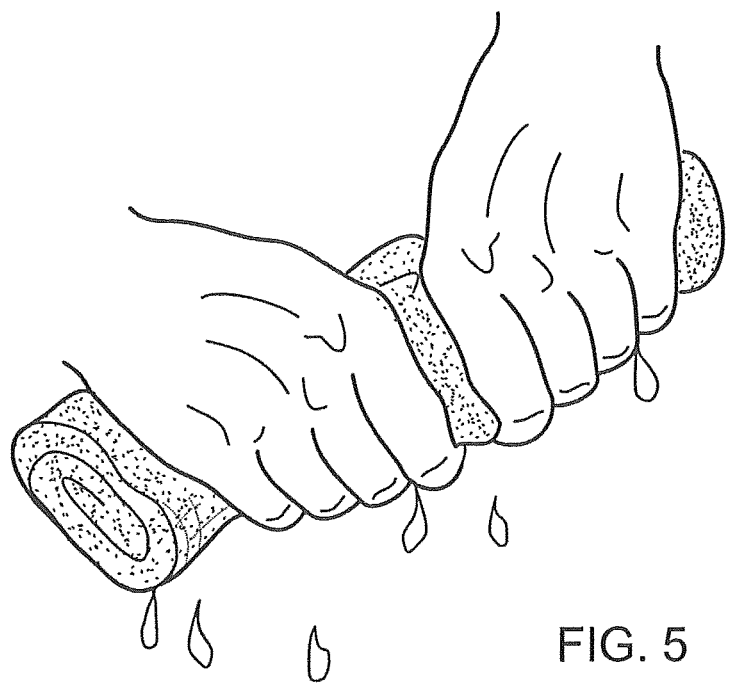
FIGS. 5 and 6 illustrate the process of removing excess moisture and smoothing the splint after wetting, respectively.
Figure 6:
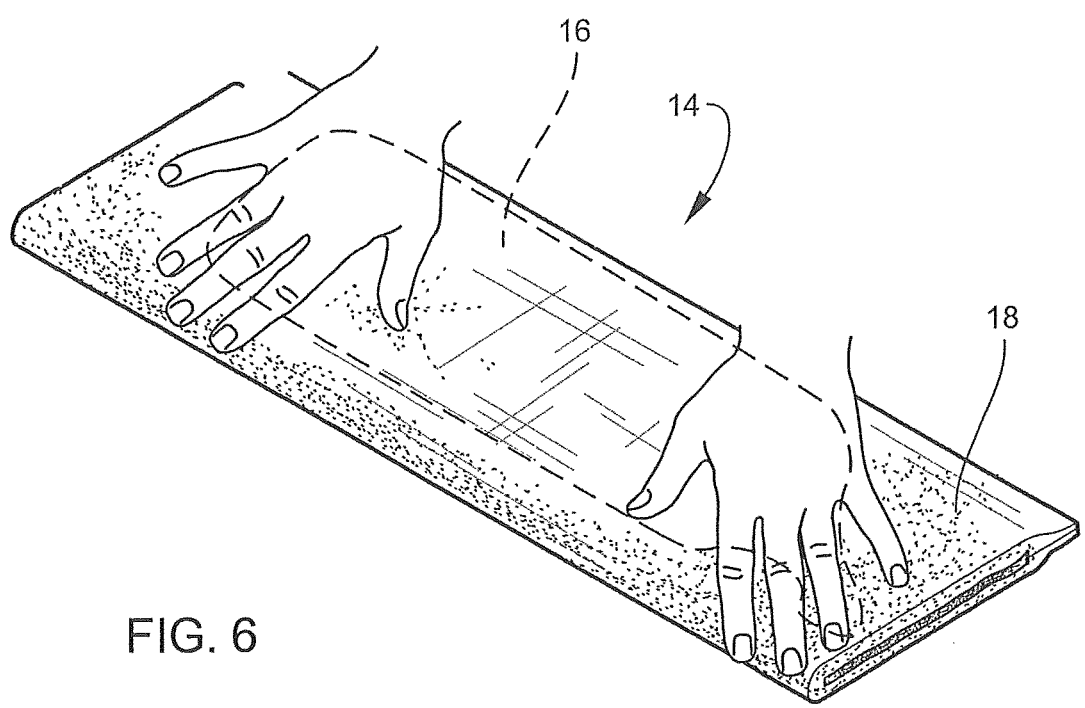

As shown in FIGS. 2 and 3, the substrate 16 is pre-cut into a shape suitable for application to a specific limb or limb part, for example an adult short arm splint, as shown. FIGS. 4, 5 and 6 illustrate a medically appropriate application technique that includes wetting the splint 14 with tepid water, FIG. 4, removing the excess water by rolling the substrate into a towel, FIG. 5, and flattening the splint 14 to prevent wrinkles when the splint 14 is applied. If desired, any excess material of the cover 18 may be trimmed.

Figure 7:
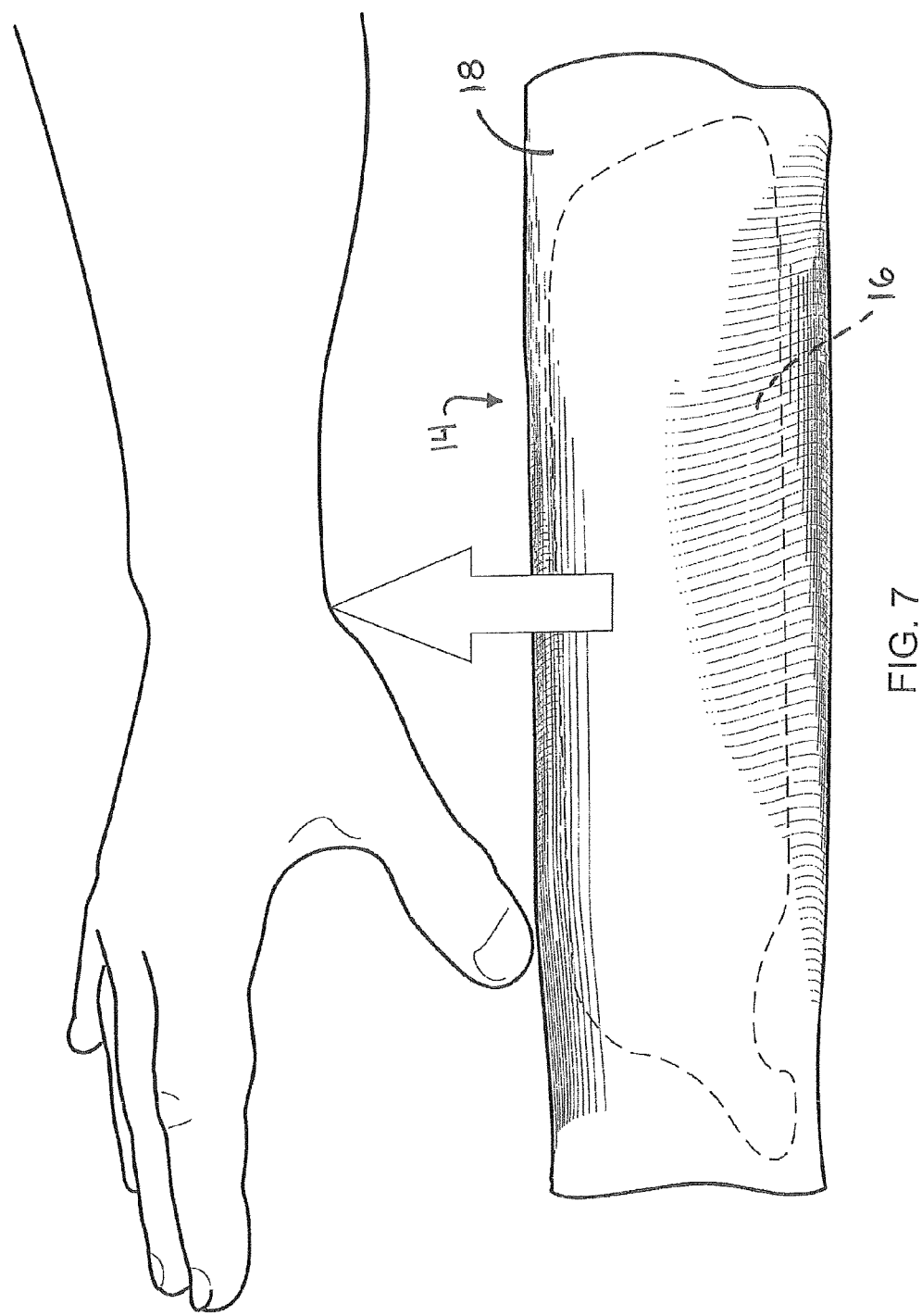
FIG. 7 shows application and molding of the splint to the medial aspect of a forearm and hand.
Figure 8:
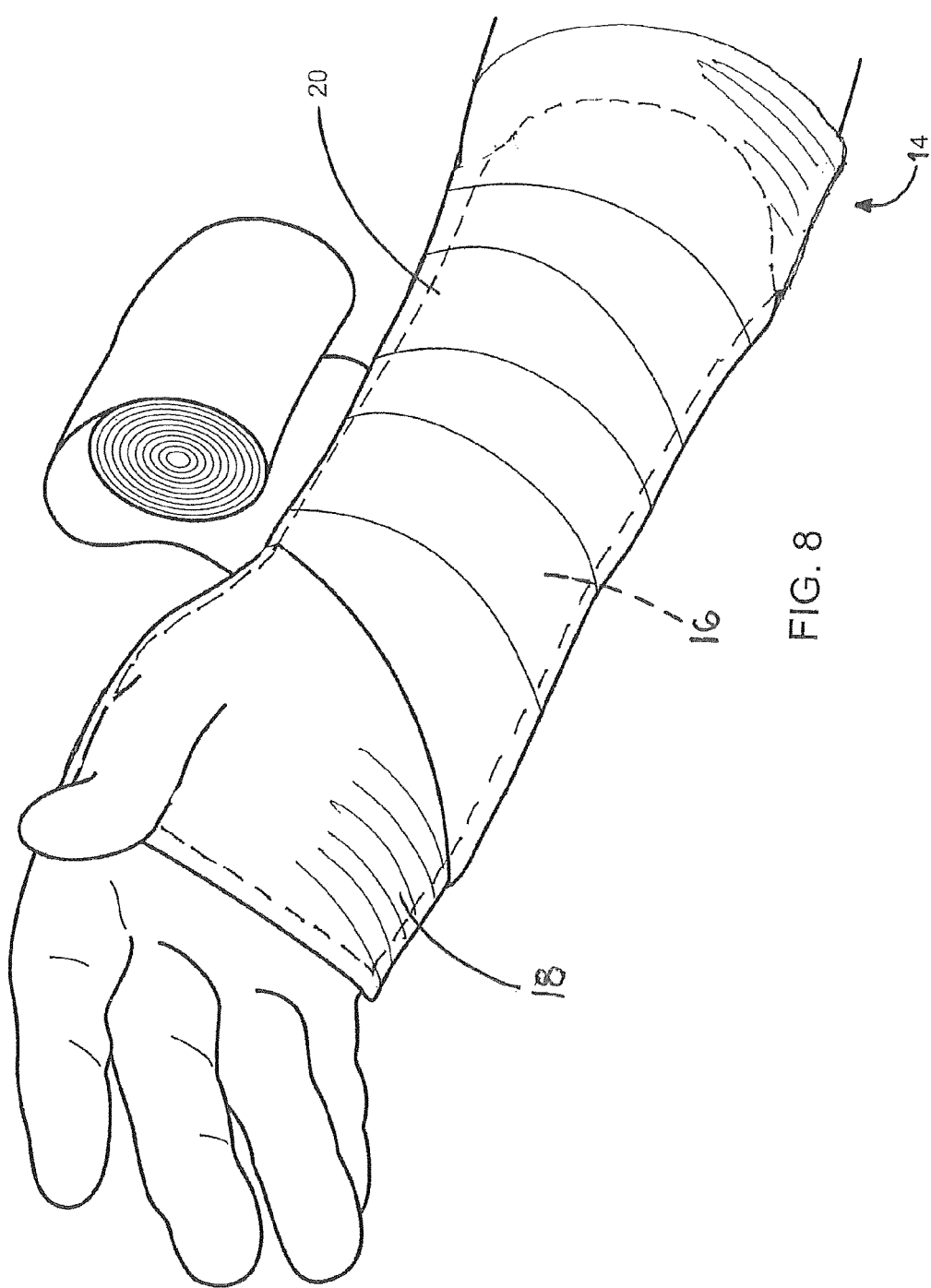
FIG. 8 shows the splint being overwrapped with an elastic bandage to hold splint in its proper shape during hardening and to retain the splint on the arm.

Referring now to FIG. 7, the splint 14 is applied to the limb and carefully molded to achieve a close conformation to the limb. This includes carefully positioning the hand and wrist as needed, and forming a distal portion of the splint 14 under the hand. As shown in FIG. 8, the splint 14 is then overwrapped with a suitable wrapping, for example, an elastic bandage 20. The bandage 20 retains the splint 14 in its molded position against the limb during hardening, and thereafter maintains the splint 14 in its supporting position against the limb during that treatment phase.

The procedure described above is intended for use during the initial, acute, phase of treatment. When severe swelling is present, a hard plaster of Paris or synthetic cast may be placed on the limb after the swelling has subsided.

Figure 9:
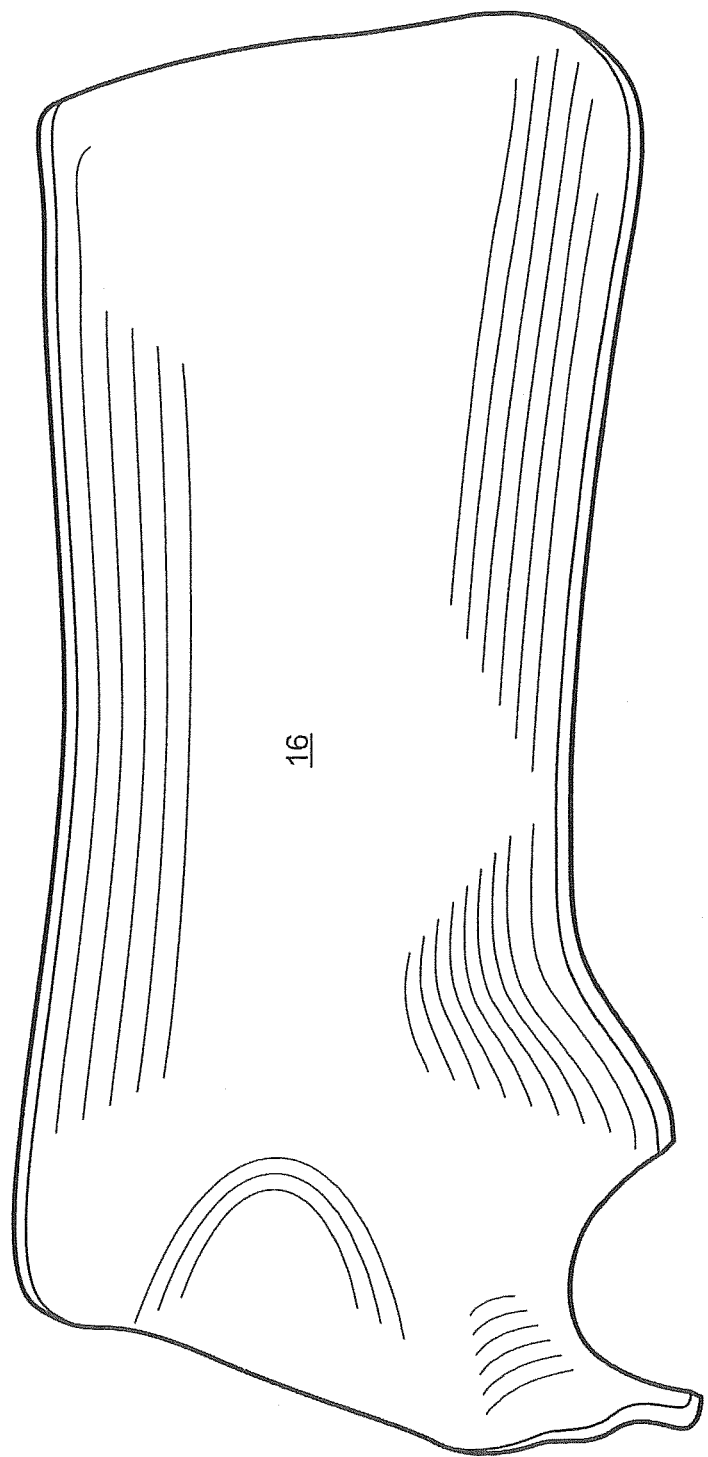
FIG. 9 shows the molded substrate after removal of the cover layer.

Whether or not a hard cast is applied, after the splint 14 is removed, it may later be reused in combination with a soft goods removable cast. As shown in FIG. 9, the cover 18 has been removed from the substrate 16, leaving only the bare substrate 16 for additional use. While it is preferable to remove the cover 18, this may not be required in all cases, the relevant issue being whether the substrate 16, with or without the cover 18, provides adequate support and conformation when used as described below.

Figure 10:
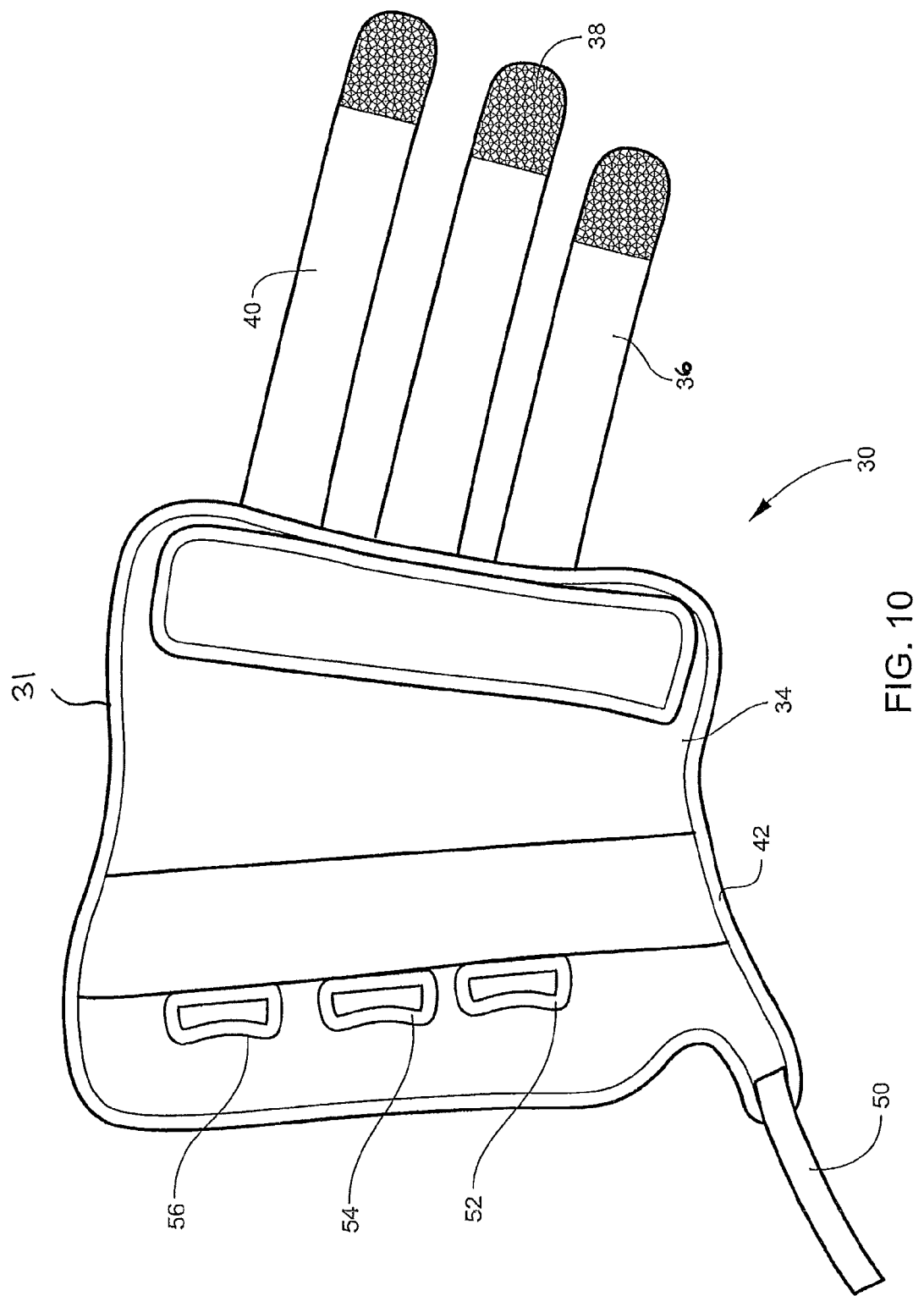
FIG. 10 is a view of the outer side of a soft goods removable cast according to a preferred embodiment of the invention.
Figure 11:
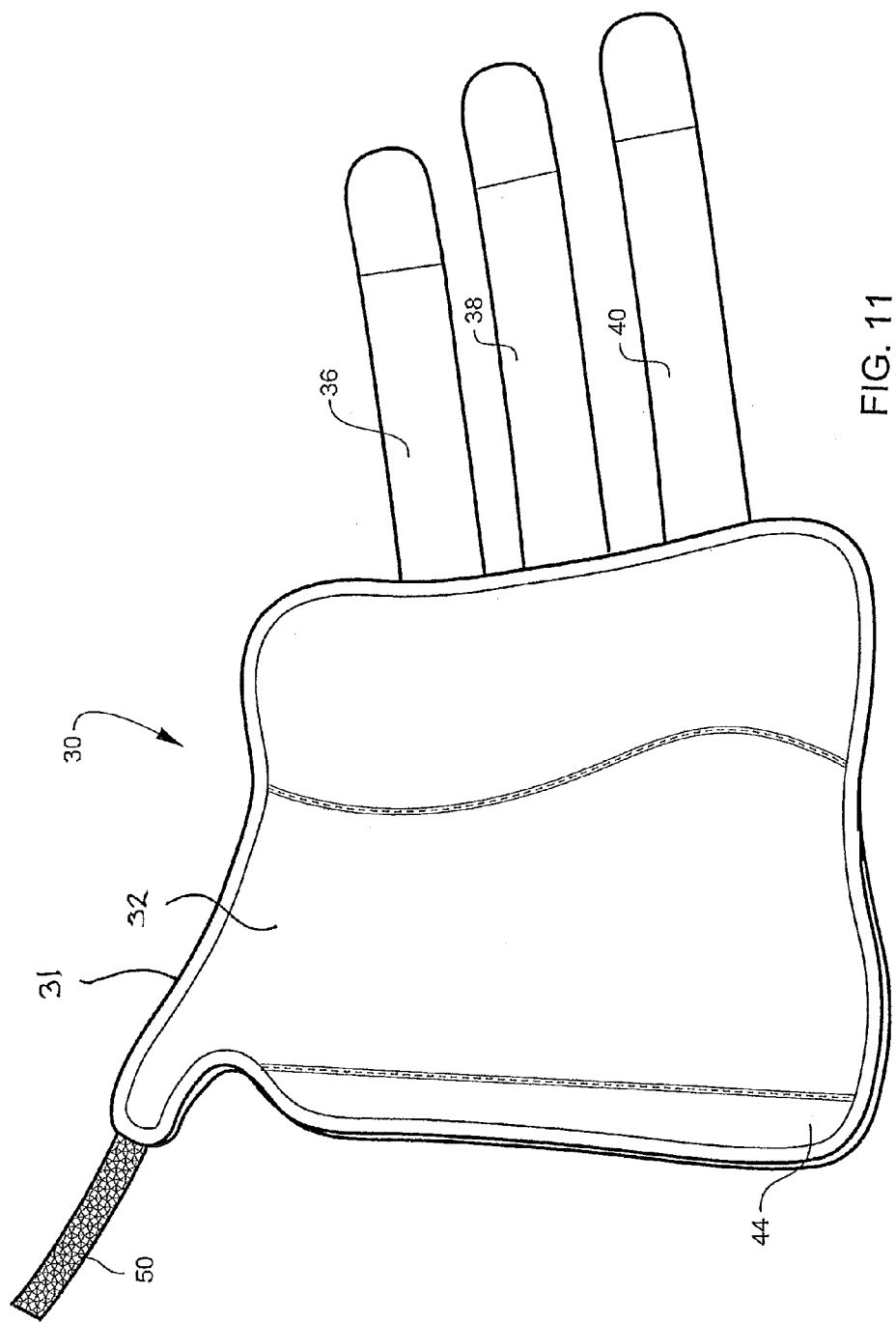
FIGS. 11-16 are sequential views showing insertion of the molded substrate into the soft goods cast and application of the cast to the forearm.
Figure 12:
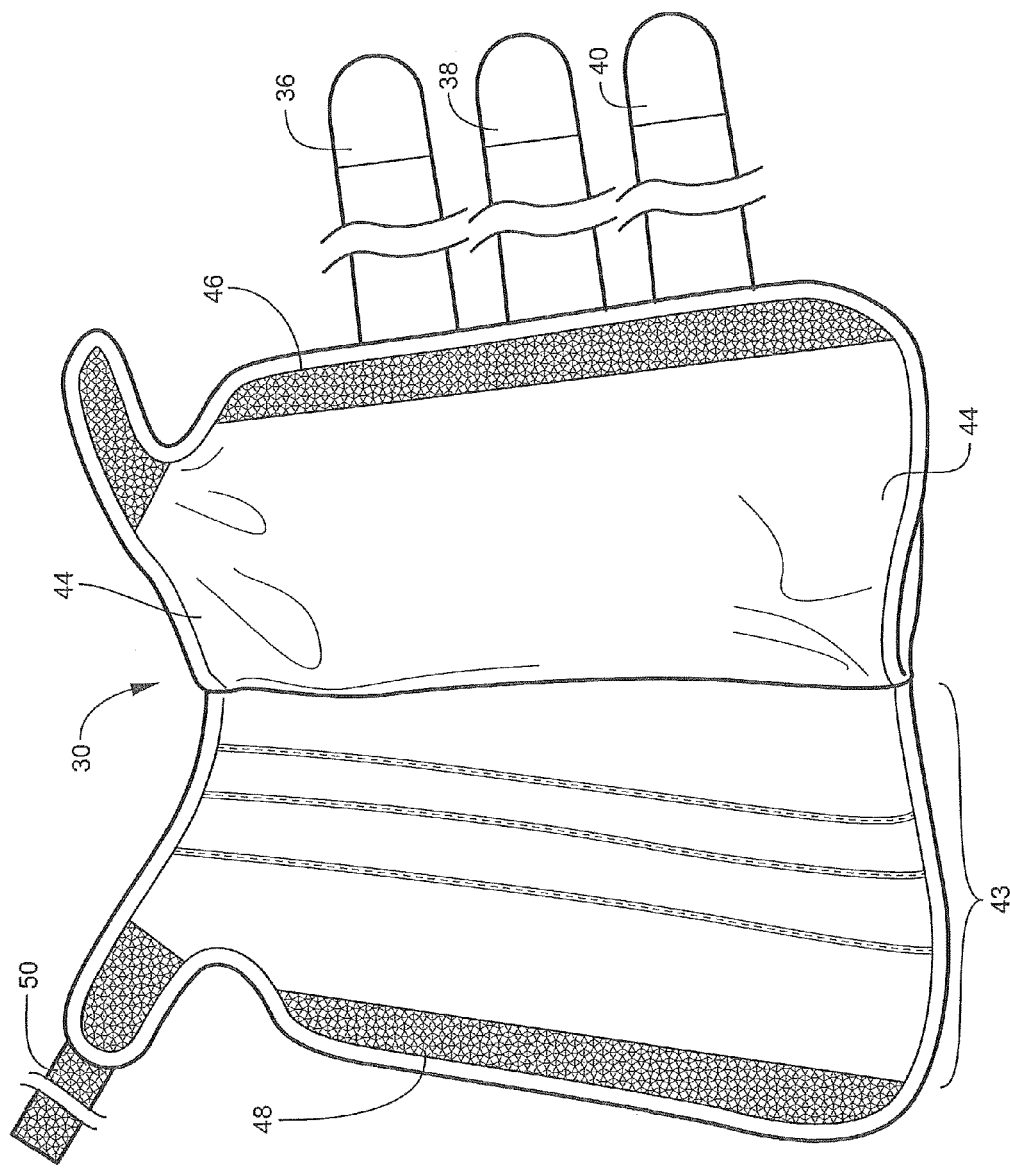

FIGS. 10 and 11 show opposite sides of a soft goods, removable cast 30 that is used in combination with the substrate 16 during post-acute and rehabilitation phases. The cast 30 includes a body 31 fabricated of a soft, conformable, stretch-knit material 32 on the interior, and an exterior fabric 34 with a loop surface for receiving complementary hooks carried by three securing straps 36, 38, 40 attached to the body 31. The interior fabric 32 and the exterior fabric 34 are bound together by an edge binding 42. The cast 30 has a light synthetic padding material sandwiched between the interior fabric 32 and the exterior fabric 34 in the bracketed area 43 in FIG. 12. The area 43 is the part of the cast 30 that directly engages the medial aspect of the arm and hand when the cast 30 is in place.

The interior of the cast 30 includes a fabric flap 44 seamed along one edge to the body 31. The flap 44 is movable between a closed position as shown in FIG. 11 and an open position shown in FIG. 12. The flap 44 includes a strip of loop material 46 fastened along its outer edge that releasably fastens to a complementary strip of hook material 48 fastened along an edge of the body 31, as shown. The cast 30 also includes an outwardly-extending hand strap 50 with a tab of hook material on the end that releasably engages the exterior loop surface of the exterior fabric 34 to close the cast 30 around the hand.

Three strap fastening rings 52, 54, 56 are attached to the exterior fabric 32 of the body 31 and cooperate with the straps 36, 38, 40, respectively, to secure the cast 30 around the forearm. The straps 36, 38, 40 are extended through respective strap fastening rings 52, 54, 56 and doubled over themselves, placing the hooks on the straps 36, 38, 40 in position to engage the exterior fabric 32.

Figure 13:
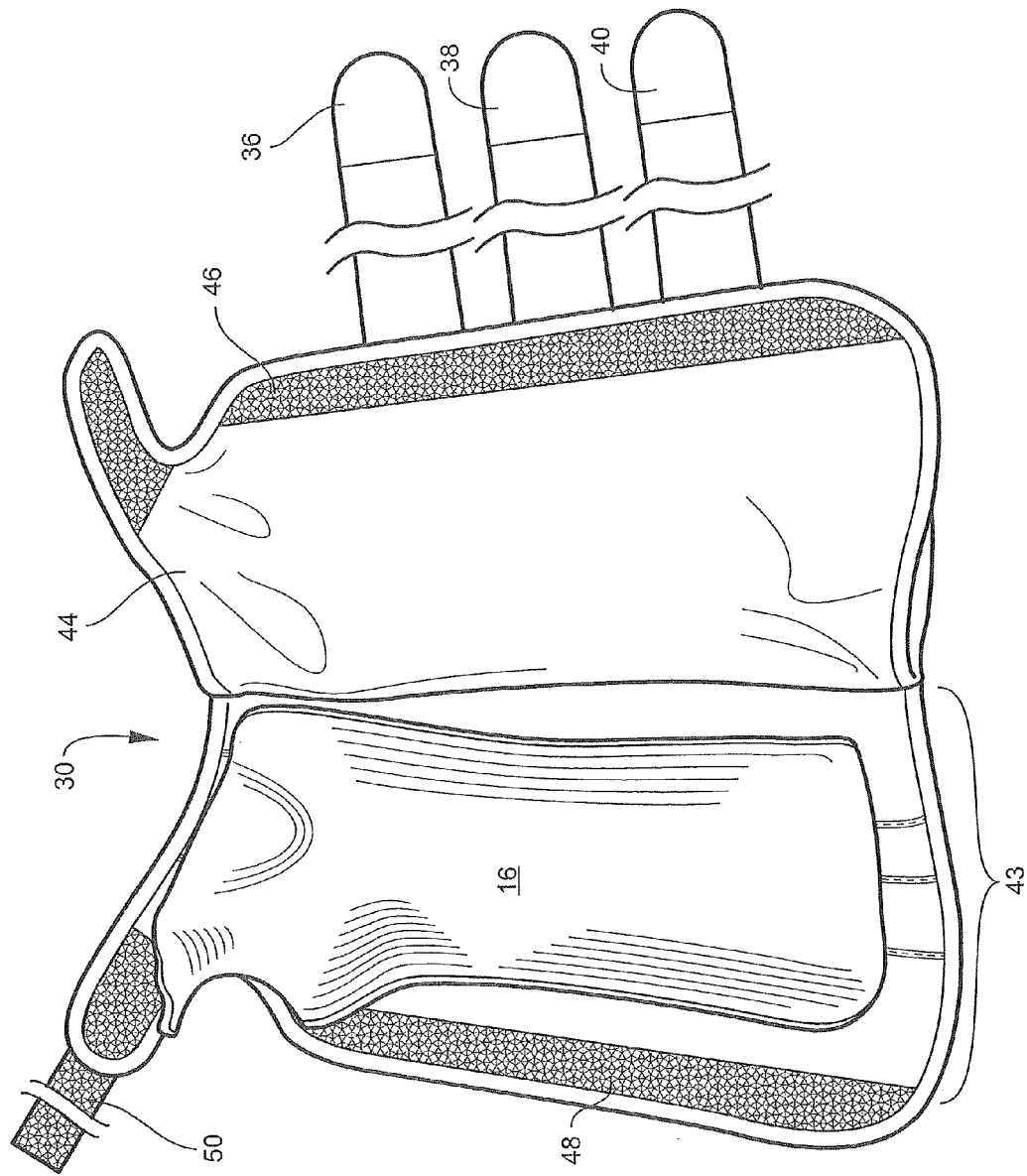
Figure 14:
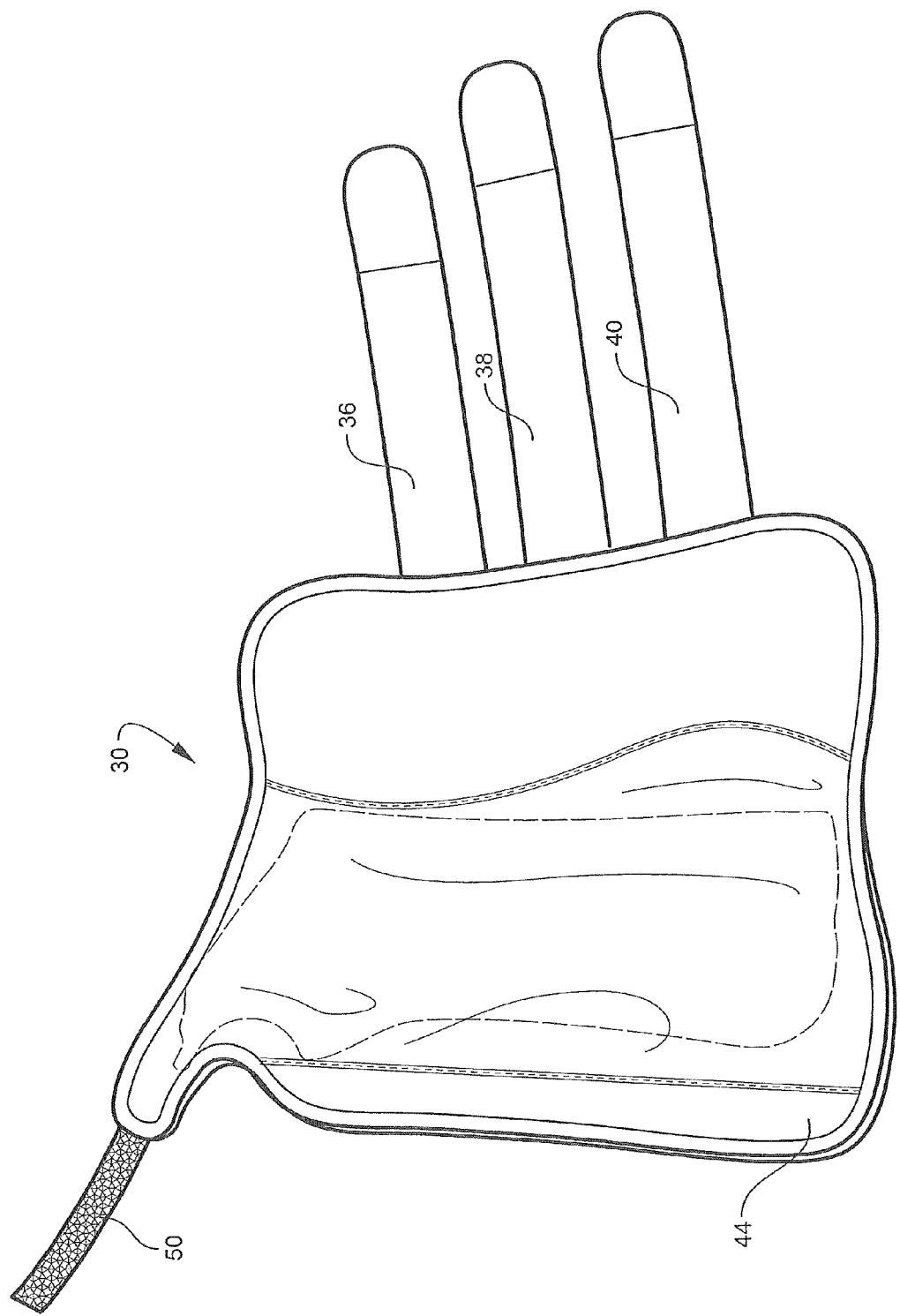
Figure 15:
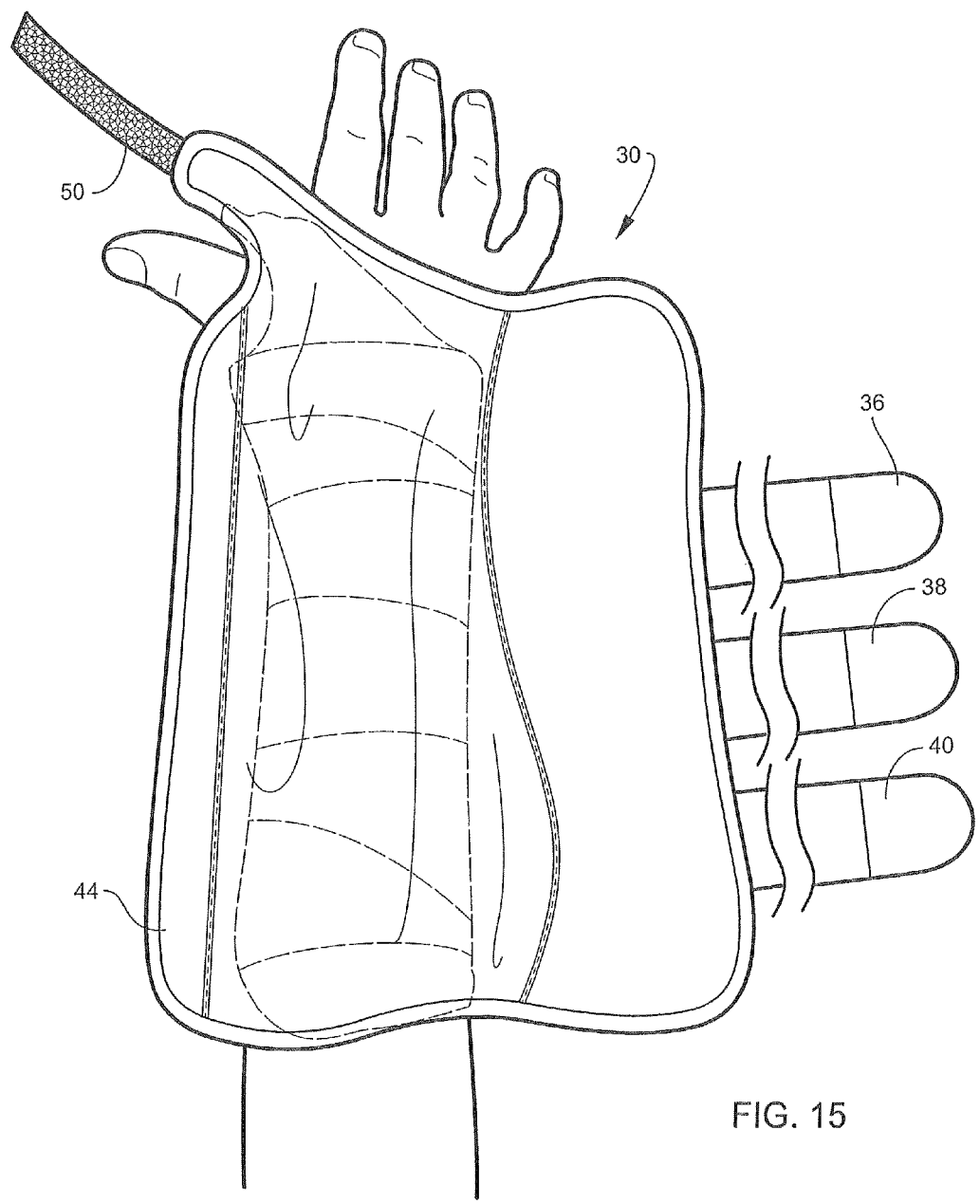
Figure 16:
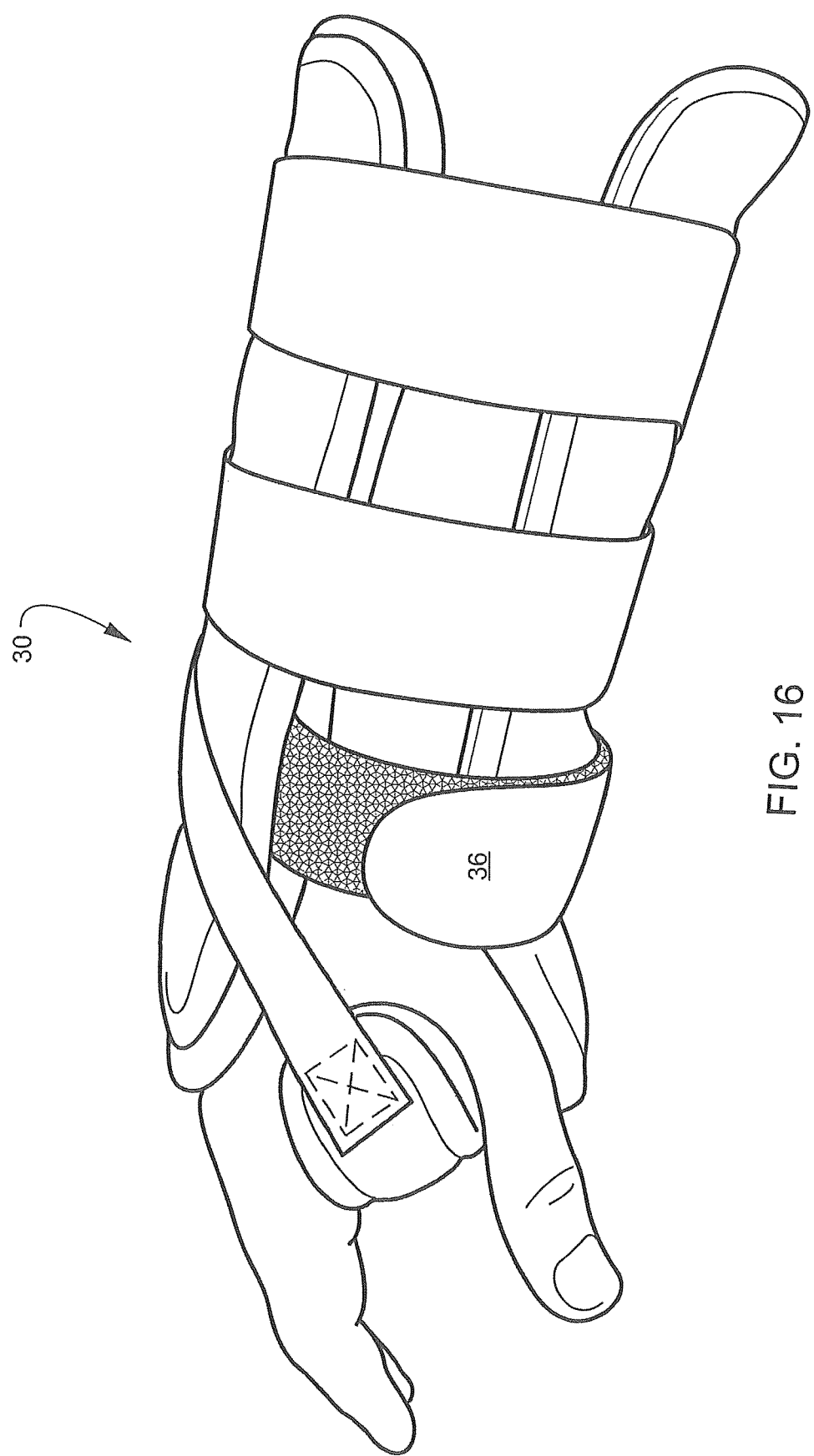

The cast 30 is prepared for use by taking the molded substrate 16, typically after removing the cover 18, and placing it in the interior of the cast 30 between the strip 46 of loop material and the strip 48 of hook material with the flap 44 in the open position, as shown in FIG. 13. The flap 44 is then folded into its closed position, FIG. 14, forming a protective pocket enclosing the substrate 16. The arm is placed over on onto the substrate 16, FIG. 15, and the cast 30 is folded around the arm and secured in place with the straps 36, 38, 40 and 50, as described above. The cast 30 provides continued support, but is easily removable and adjustable as needed during the remainder of the healing process. Because the original molded substrate 16 is reused, a proper fit is insured while avoiding the cost of supplying and applying another splint for use with the cast 30.

Figure 17:
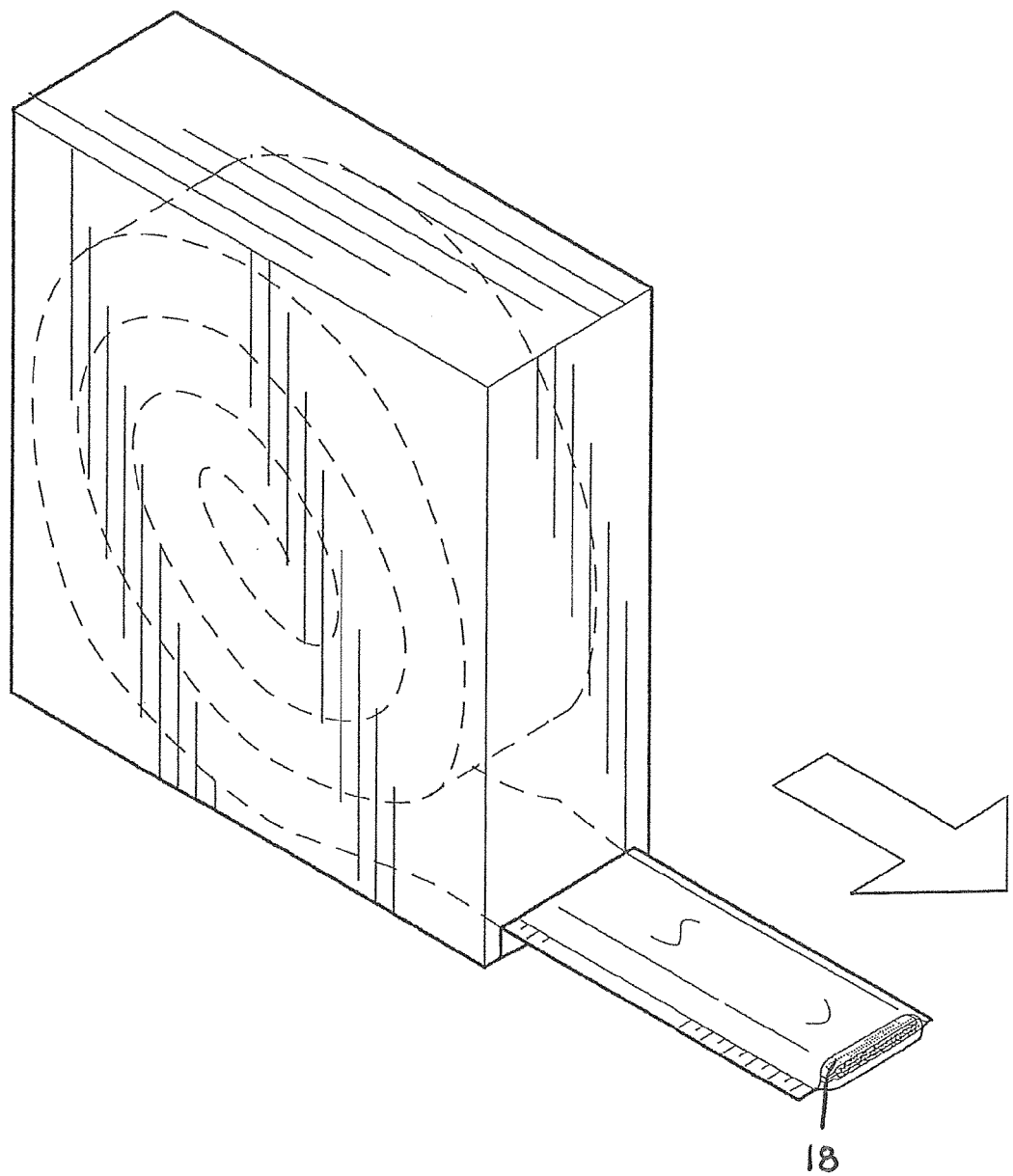
FIG. 17 illustrates a roll-form type of splint and packaging suitable for use in accordance with the invention.
Figure 18:
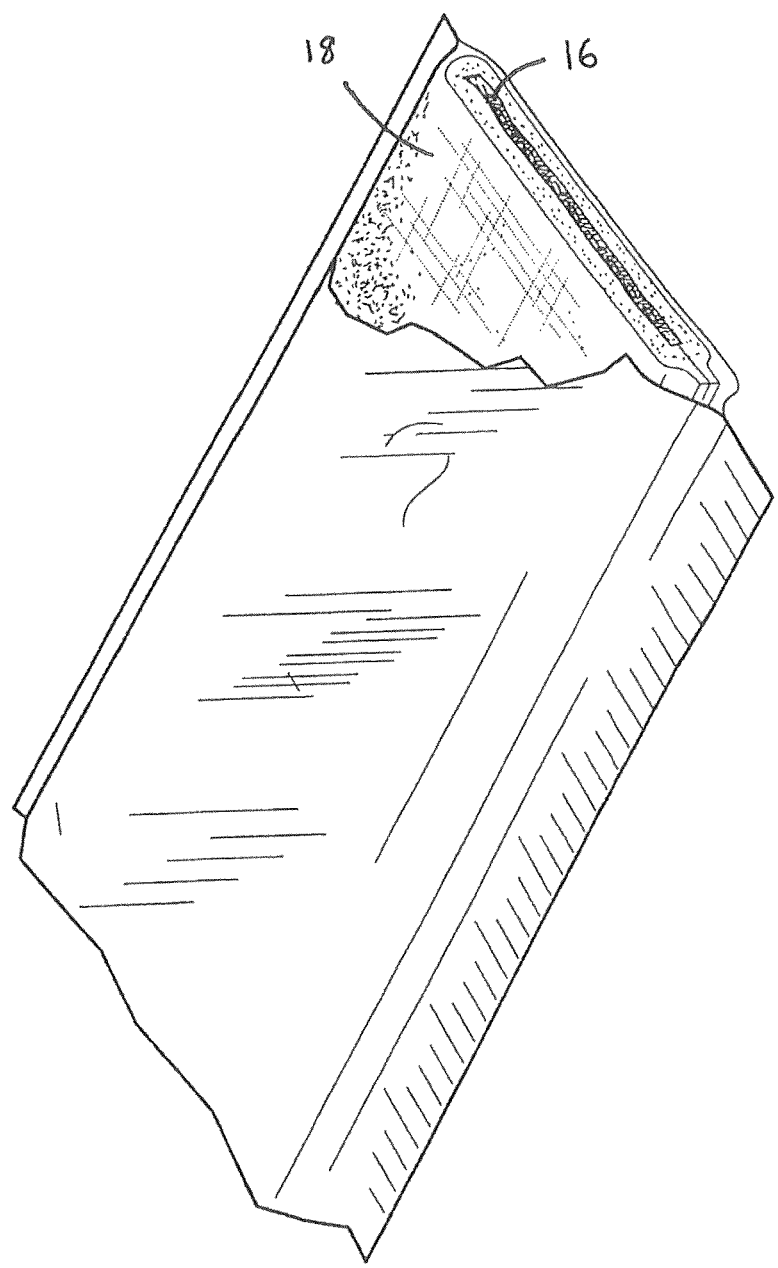
FIG. 18 illustrates a length of roll-form splint material removed from the coil of material shown in FIG. 17.

As shown in FIGS. 17 and 18, a roll-form type of splint material may be used as an alternative to the pre-cut splint 14 described above. This type of splint material is fully described in applicant's U.S. Pat. No. 4,770,299. As described above, the splint is prepared and applied to the patient as a splint during an acute phase of treatment. Thereafter, the cover surrounding the substrate is preferably removed, and the molded substrate is mated with the cast 30, also as described above.

Figure 19:
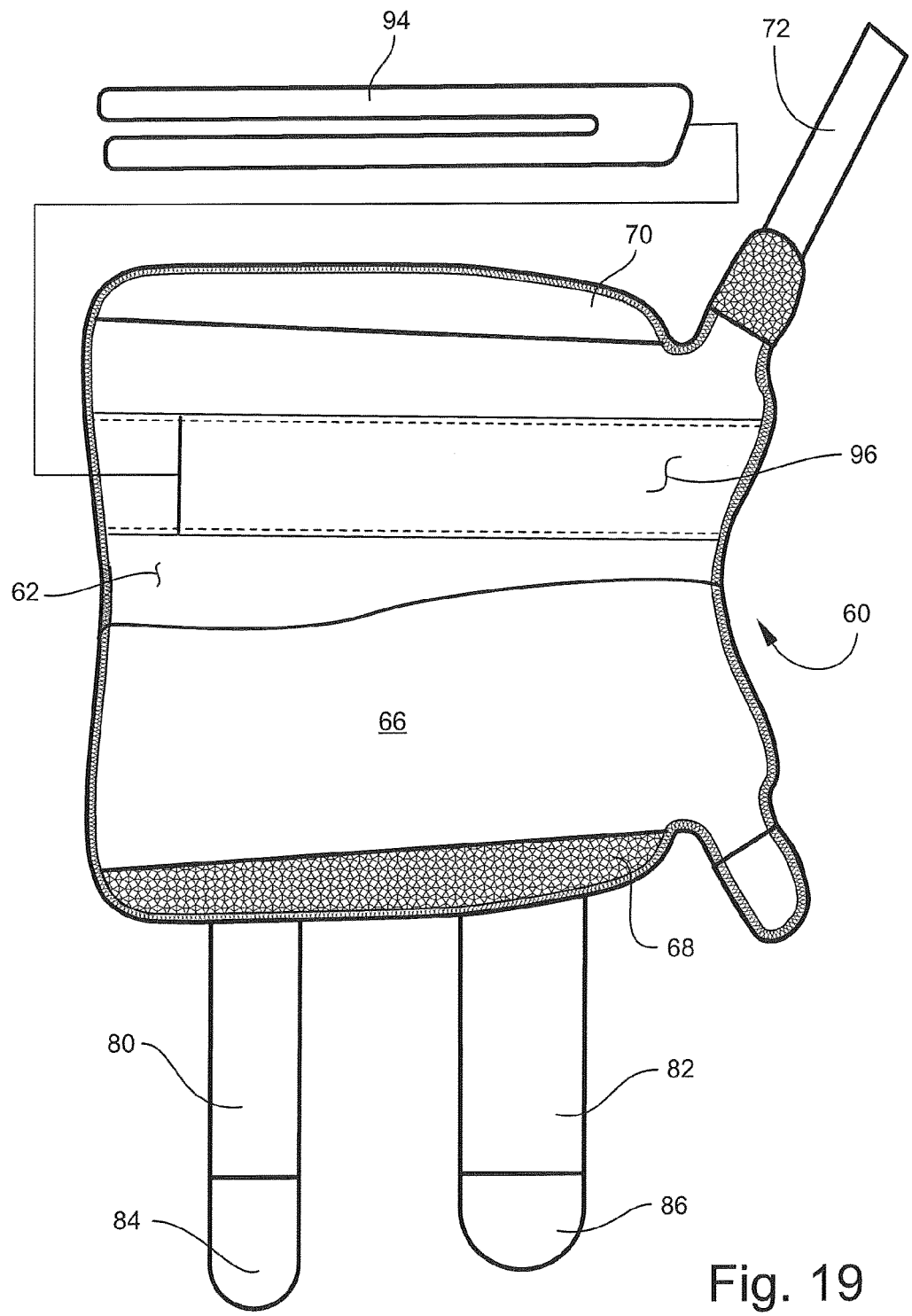
FIG. 19 is a top plan view of the inner side of a soft goods removable cast according to a further preferred embodiment of the invention.
Figure 20:
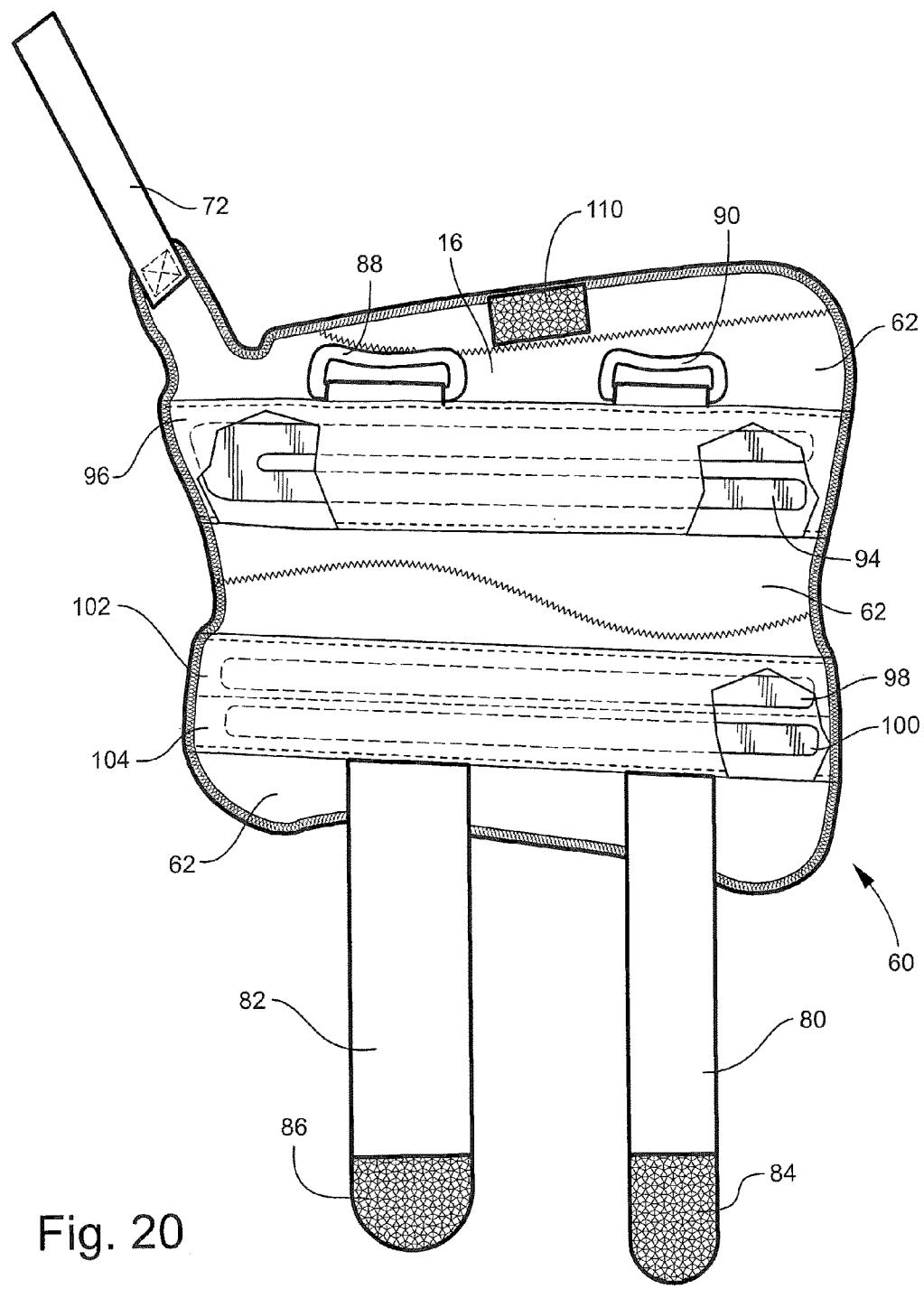
FIG. 20 is a top plan view of the outer side of the soft goods removable cast shown in FIG. 19.

Referring now to FIGS. 19-25, a modified embodiment is illustrated with particular reference to the material from which the body of the cast is fabricated. Instead of a conventional medical fabric, the body of the cast is formed of a three-dimensional knitted fabric that is very lightweight. As shown in FIGS. 19 and 20, opposite sides of a soft goods, removable cast 60 is shown that is used in combination with the substrate 16 during post-acute and rehabilitation phases, as described above. The cast 60 includes a body 62 fabricated of a soft, conformable, single layer, three-dimensional double bar knitted fabric engineered to provide enhanced moisture transfer from the skin outwardly into the atmosphere. The specifications for the fabric 64 are as set out below:

Moisture transfer rate (MVTR) of between 500 and 600 g/m$^2$/24 hrs, and preferably about 560. g/m$^2$/24 hrs.

Threading:

| | |
|---|---|
| Bar 1 | Fully threaded polypropylene monofil 0.1 mm, 2190 mm/rack inlay over 4 needles. |
| Bar 2 | Fully threaded polypropylene 100 Denier flat thread, 2550 mm/rack chain stitch. |
| Bar 3 | Half threaded polypropylene monofil 0.1 mm, 8200 mm/rack 3 needle "V" stitch. |
| Bar 4 | Half threaded polypropylene monofil 0.1 mm, 8655 mm/rack 5 needle "V" stitch. |
| Bar 5 | Half threaded polypropylene monofil 0.1 mm, 2060 mm/rack 3 chain stitch. |
| Bar 6 | Half threaded polypropylene monofil 0.1 mm, 1590 mm/rack inlay over 3 needles. |
| | 690 courses/m; 4 mm thick in relaxed state; weight = 190 g/m$^2$. |

Figure 21:
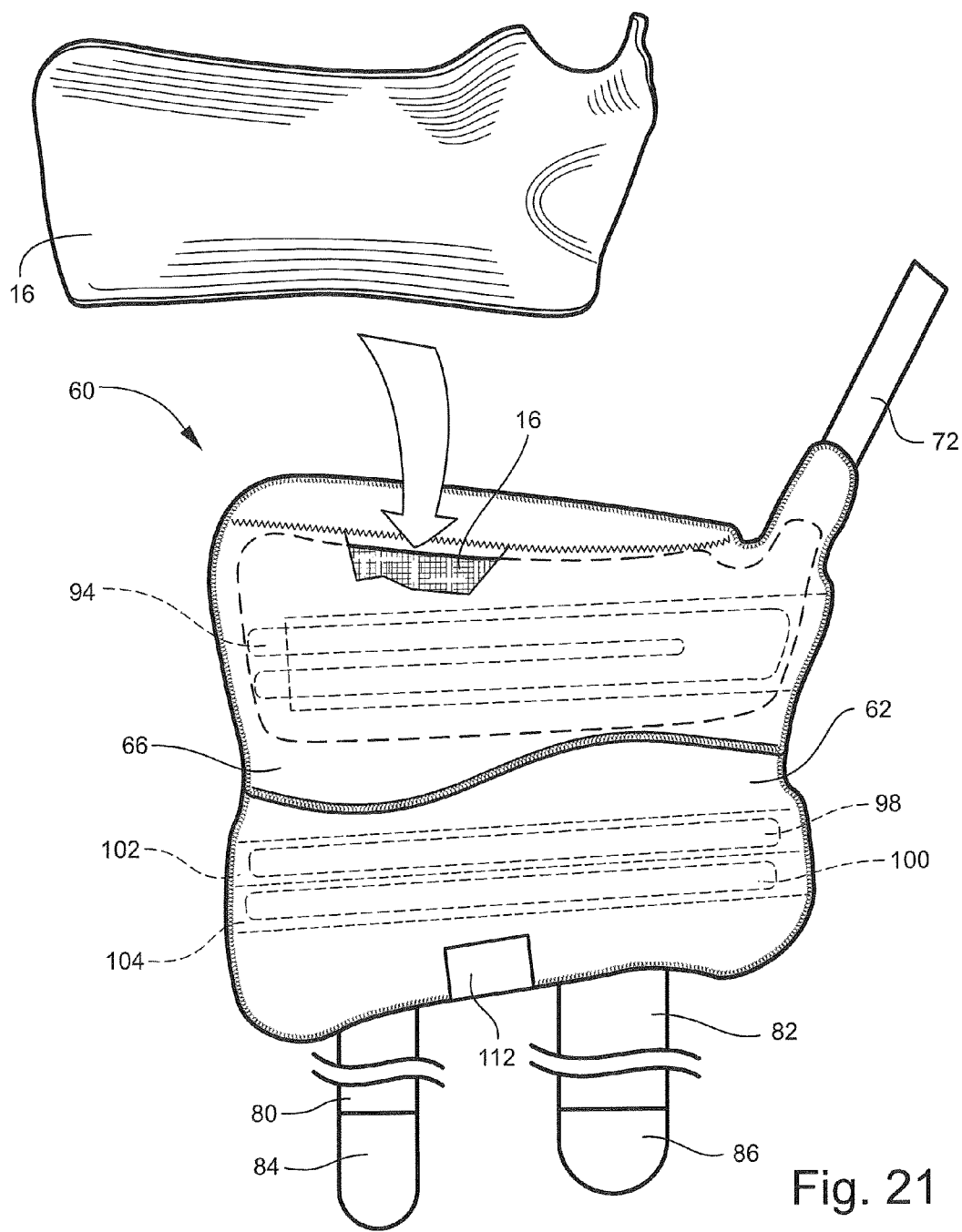
FIG. 21 is a top plan view of the outer side of the soft goods removable cast shown in FIG. 19, showing placement of stiffening elements in the structure of the cast.
Figure 22:
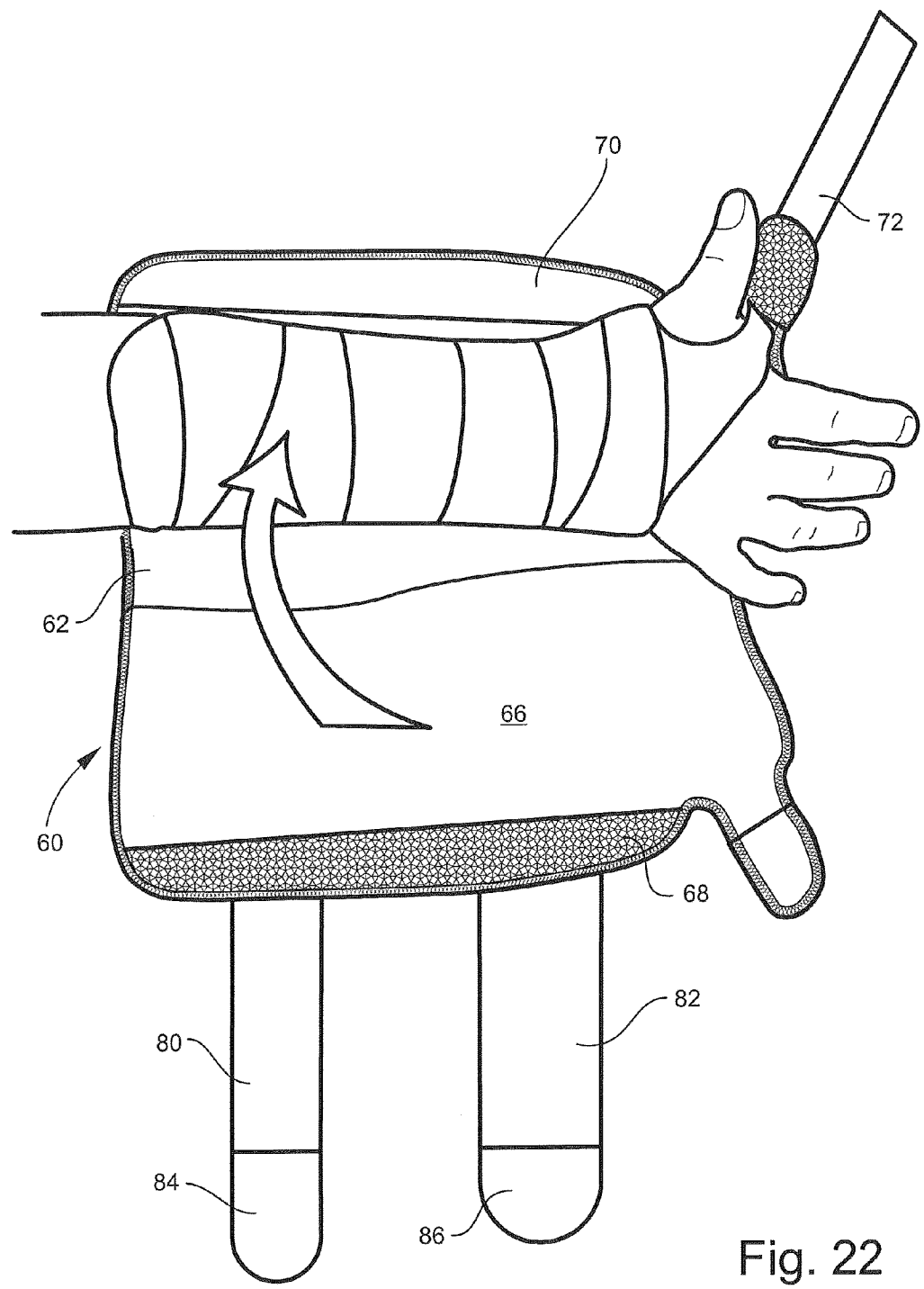
FIG. 22 is a top plan view showing placement of the cast onto a forearm.
Figure 23:
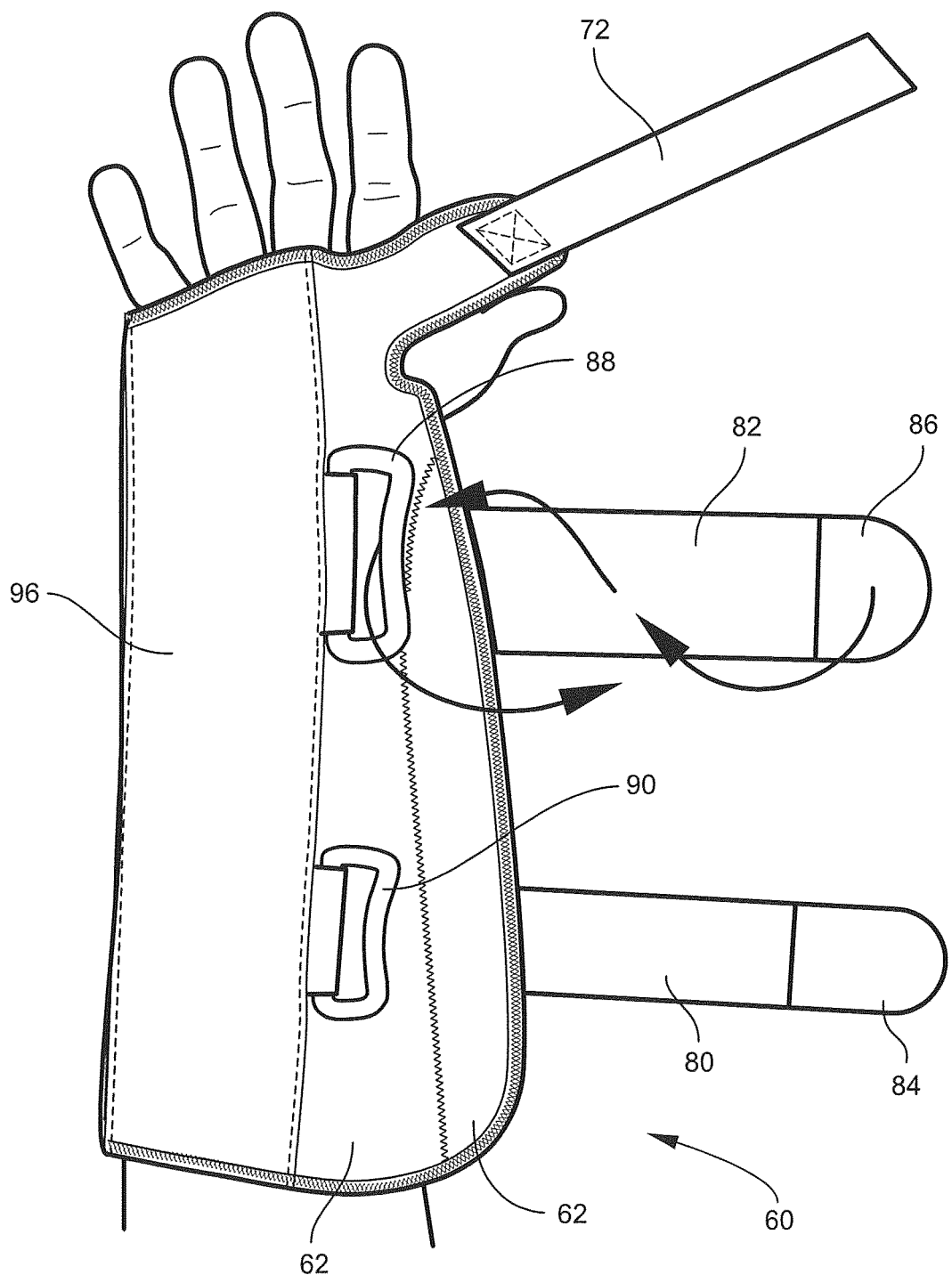
FIGS. 23-25 are further views showing placement and securement of the cast onto the forearm.

In contrast to the cast 30 described above, the fabric of the body 62 is a single layer. The interior of the cast 60 includes a fabric flap 66 seamed along one edge to the body 62. The flap 66 is movable between an open position shown in FIGS. 19 and 22, and a closed position as best shown in FIG. 21. The flap 66 includes a strip of hook material 68 fastened along its outer edge that releasably fastens to a complementary strip of loop material 70 fastened along an edge of the body 62, as shown. When attached as described the flap 66 forms a pocket in which the molded substrate 16 is placed, as shown in FIGS. 19, 20 and 21. The flap 66 then forms a padding surface against which the forearm rests.

Figure 24:
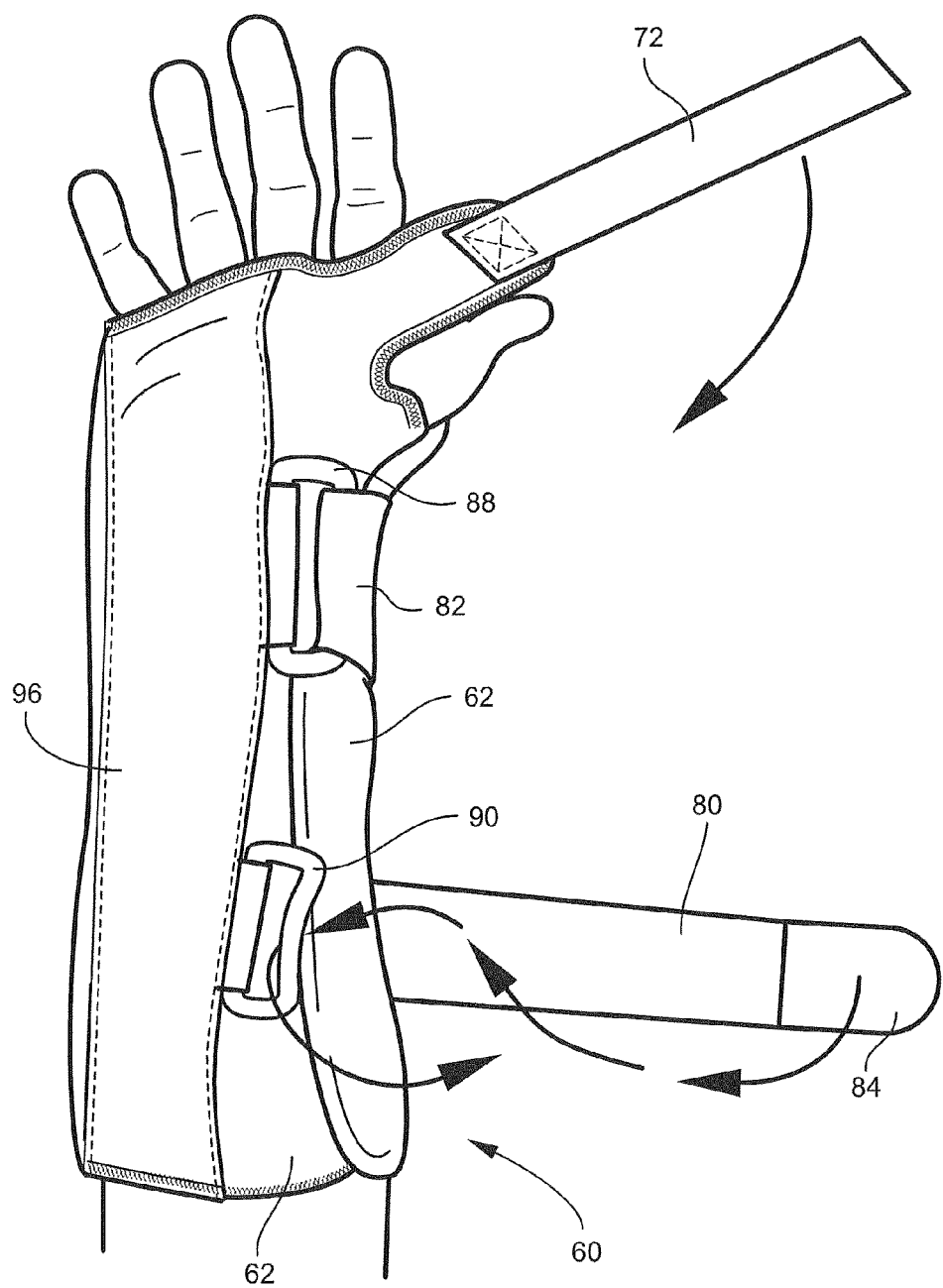
Figure 25:
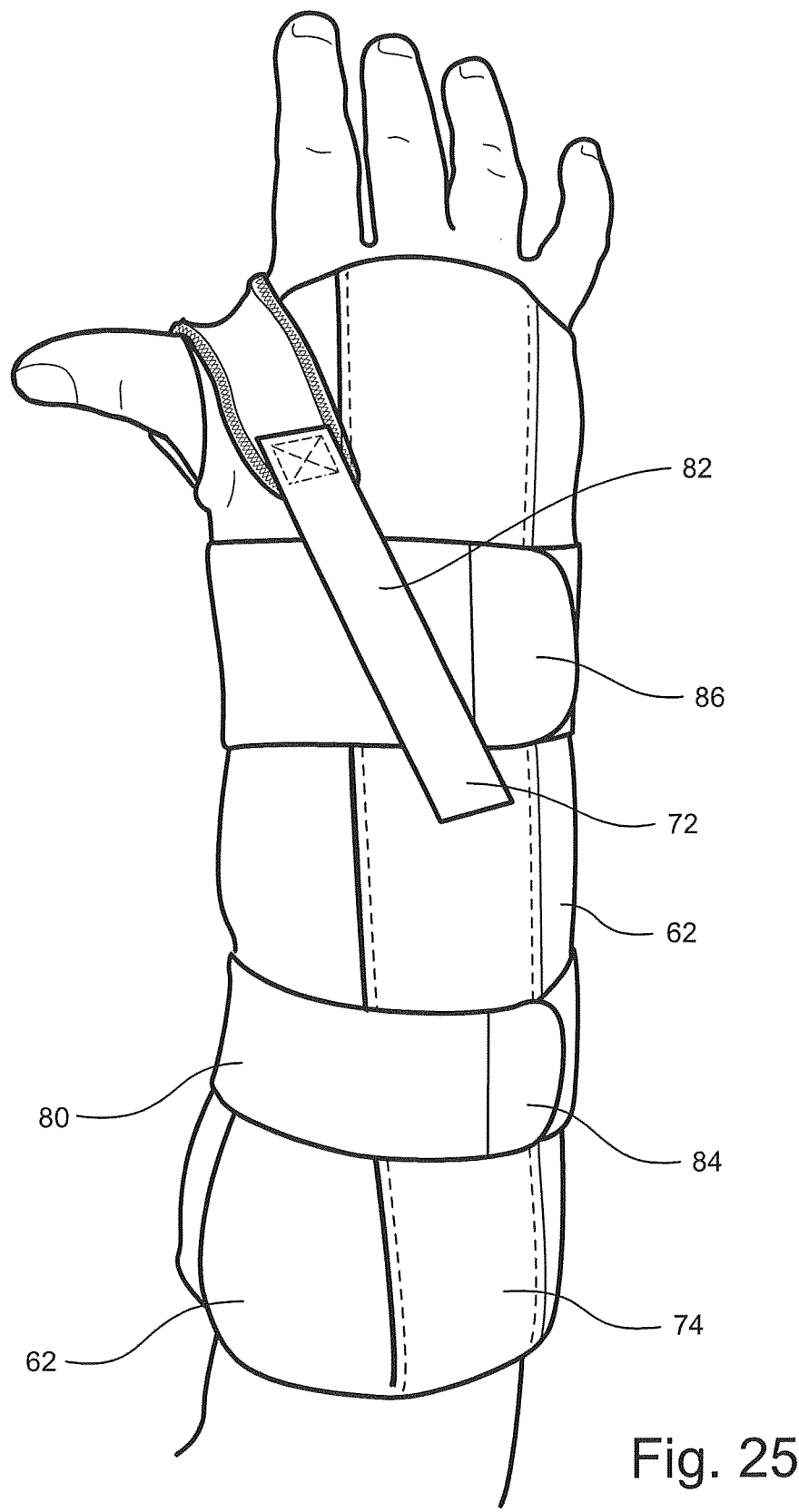

The cast 60 also includes an outwardly-extending hand strap 72 of hook material that releasably engages an exterior strip 74 of loop material on the outer side of the cast 60, as best shown in FIG. 20. The hand strap 72 is used to assist in closing the cast 60 around the hand, as shown in FIGS. 24 and 25.

Two straps 80, 82 are stitched to the body 62 and include patches of hook material 84, 86 on their respective ends. Strap fastening rings 88, 90 are attached to the exterior fabric of the body 62 and cooperate with the straps 82, 80, respectively, to secure the cast 60 around the forearm. The straps 80, 82 are extended through respective strap fastening rings 88, 90 and doubled over themselves and secured to the exterior strip 74 of loop material. See FIG. 23.

Further stiffening and conformability is provided by a bendable U-shaped insert 94 that slips into an elongate pocket 96. The insert 94 overlies the substrate 16 and is conformable to the shape of the substrate 16 along its length. Preferably, the insert 94 is fabricated of metal, such as aluminum, that is thin enough to bend into the desired shape but thick and resilient enough, for example, 1-2 mm, to hold its shape under normal use.

In addition, a pair of elongate stiffeners 98, 100 are positioned in pockets 102, 104 that extend substantially the entire length of the body 62. The stiffeners 98, 100 are principally intended to maintain the body 62 in a relatively flat, open and extended condition during assembly of the cast 60 and during wear. The outer surface of the pockets 102, 104 is loop material 74 and mates with the hook material on the strap 72, as shown in FIG. 25.

The cast 60 is prepared for use by taking the molded substrate 16, typically after removing the cover 18, and placing it in the interior of the cast 60 with the flap 66 in the open position, as shown in FIG. 19. The flap 66 is then folded into its closed position, FIG. 21, forming a protective pocket enclosing the substrate 16. The arm is placed in the trough formed by the substrate 16, and the cast 60 is folded around the arm and secured in place with the straps 72, 80 and 82, as described above. The cast 60 may be held in place temporarily during placement of the straps 72, 80 and 82 by attaching a small patch of hook material 110 on one edge of the cast 60 to a small patch of loop material 112 on the opposite face and edge of the cast 60. See FIGS. 20 and 21.

Sequential views of the cast 60 being applied to a forearm are shown in FIGS. 22-25.

Figure 26:
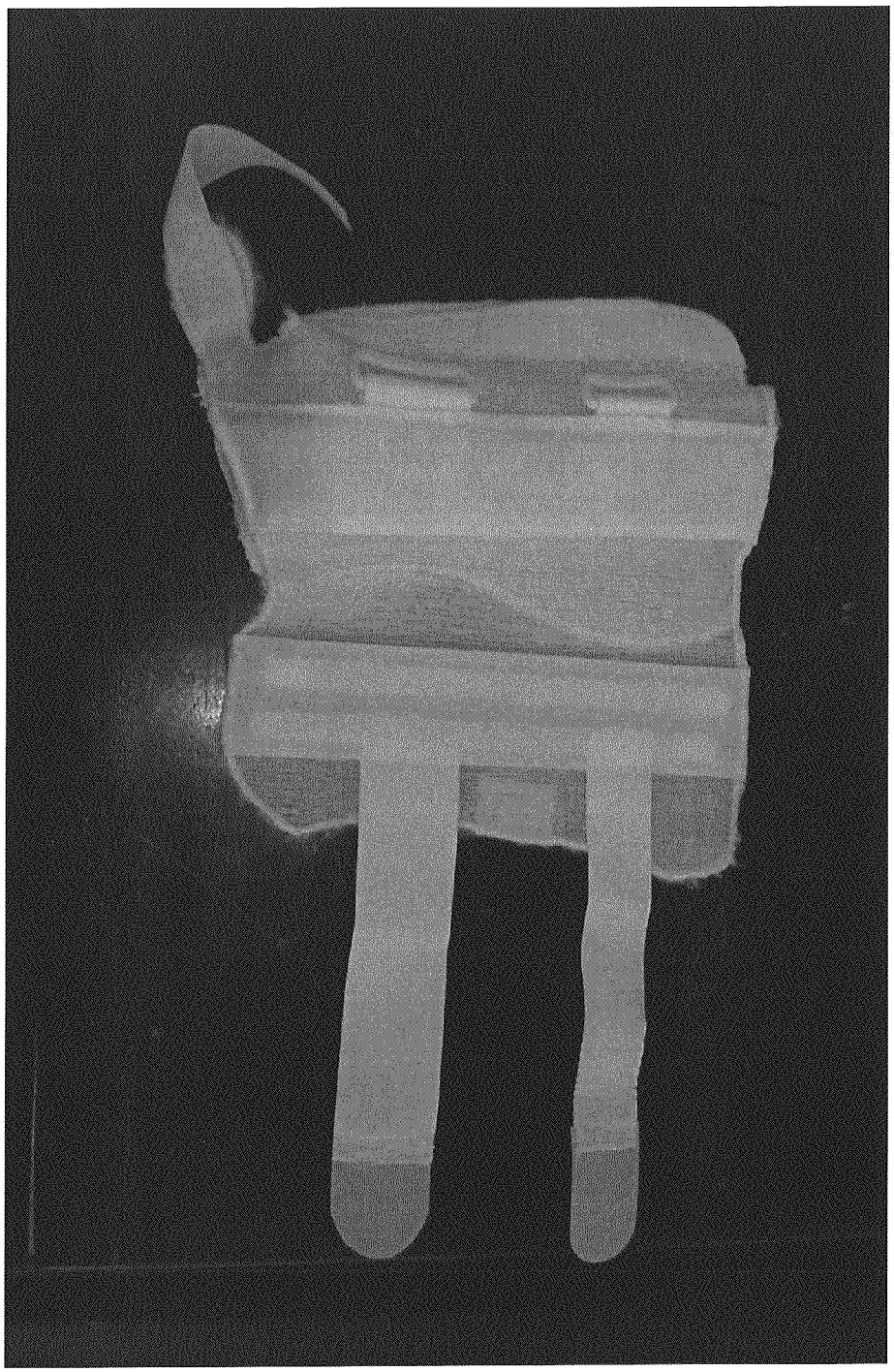
FIGS. 26 and 27 are photographic representations of the outside and inside, respectively, of the cast of FIGS. 19-25, for providing detail regarding the surface materials and textures.
Figure 27:
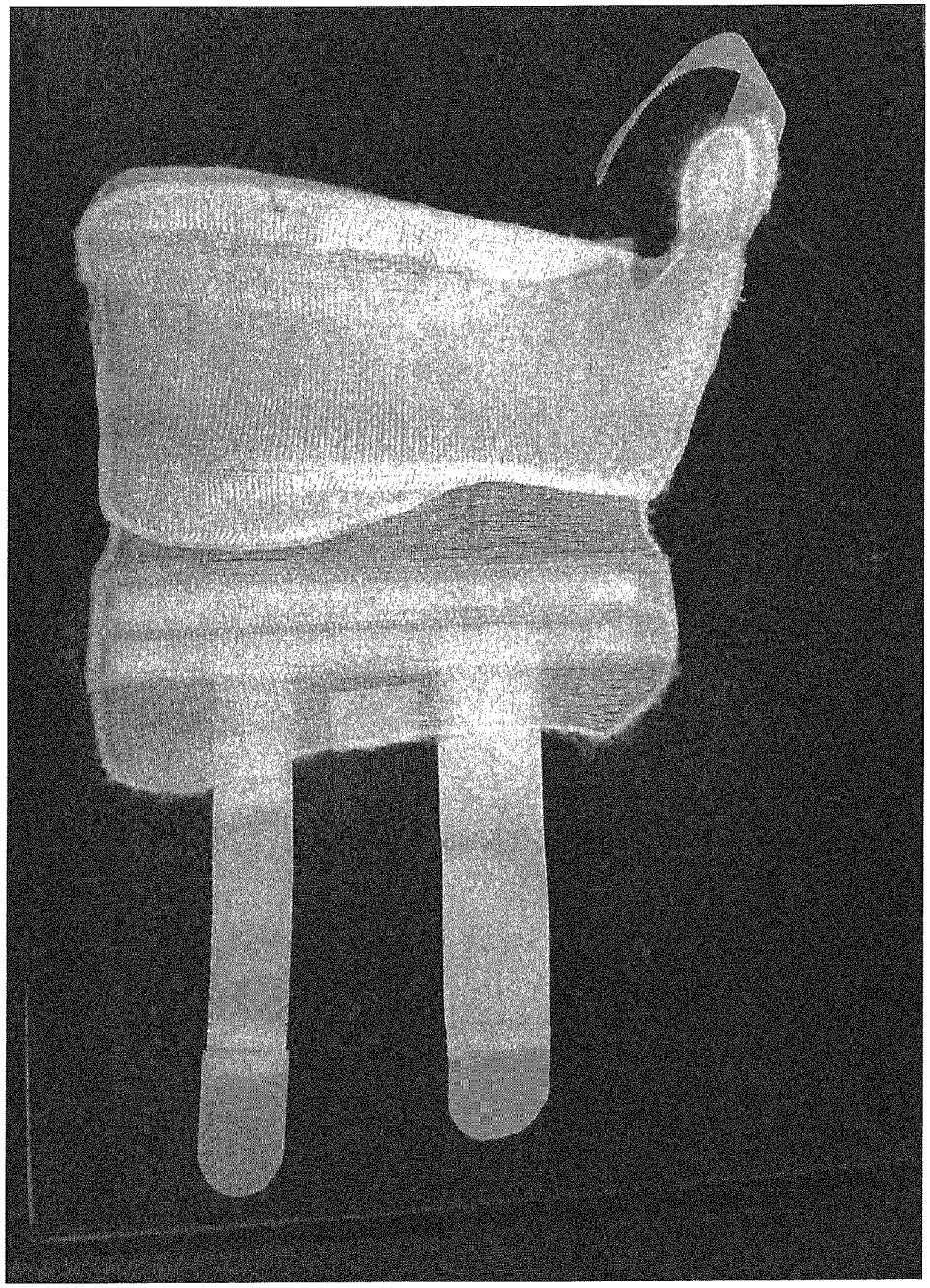

FIGS. 26 and 27 are photographic representations of the outside and inside, respectively, of the cast 60 for providing detail regarding the surface materials and textures.

The cast 60 provides continued support, but is easily removable and adjustable as needed during the remainder of the healing process. Because the original molded substrate 16 is reused, a proper fit is insured while avoiding the cost of supplying and applying another splint for use with the cast 60.

Figure 28:
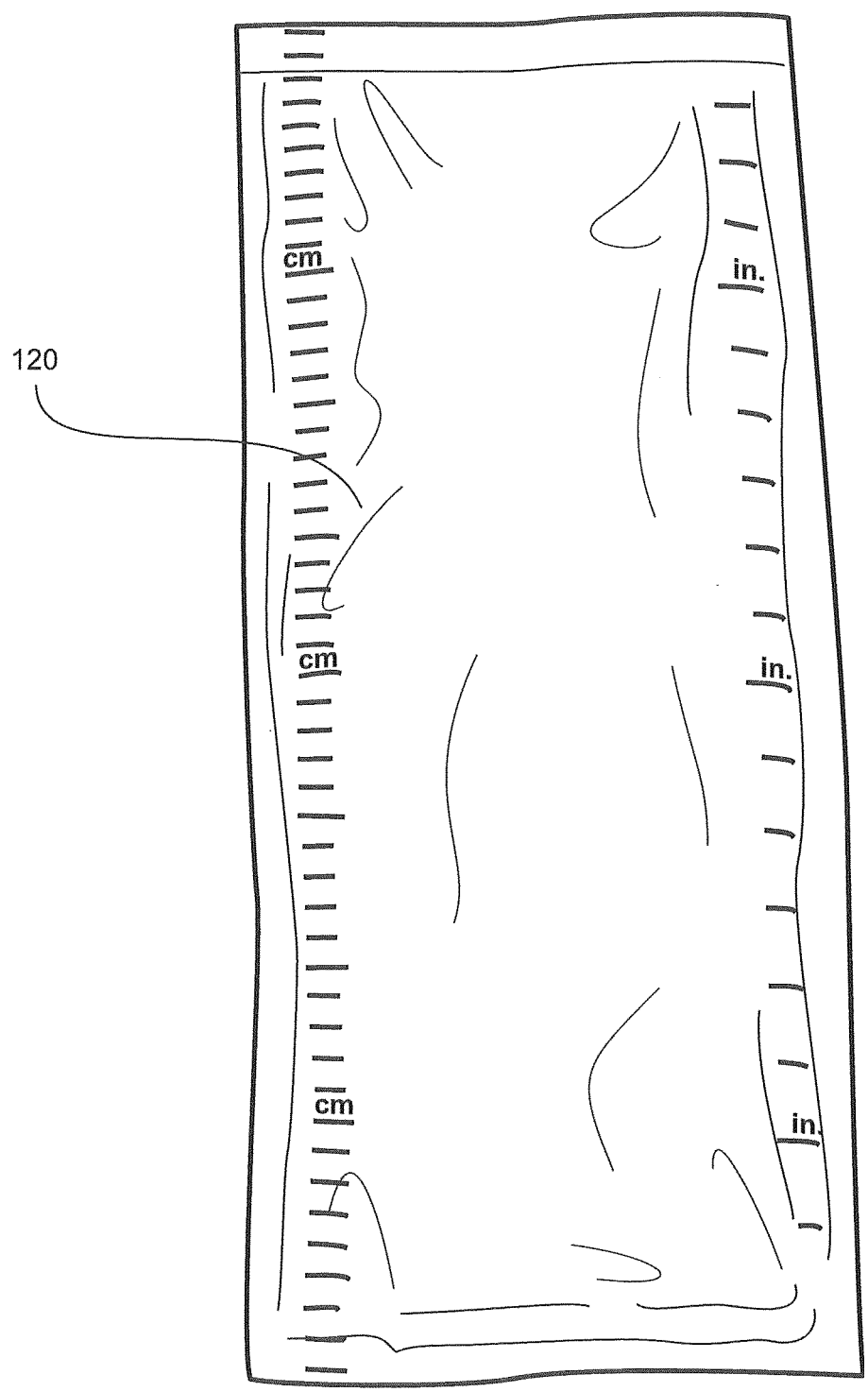
FIG. 28 is a view of a moisture-impervious package in which the cast may be stored until use.
Figure 29:
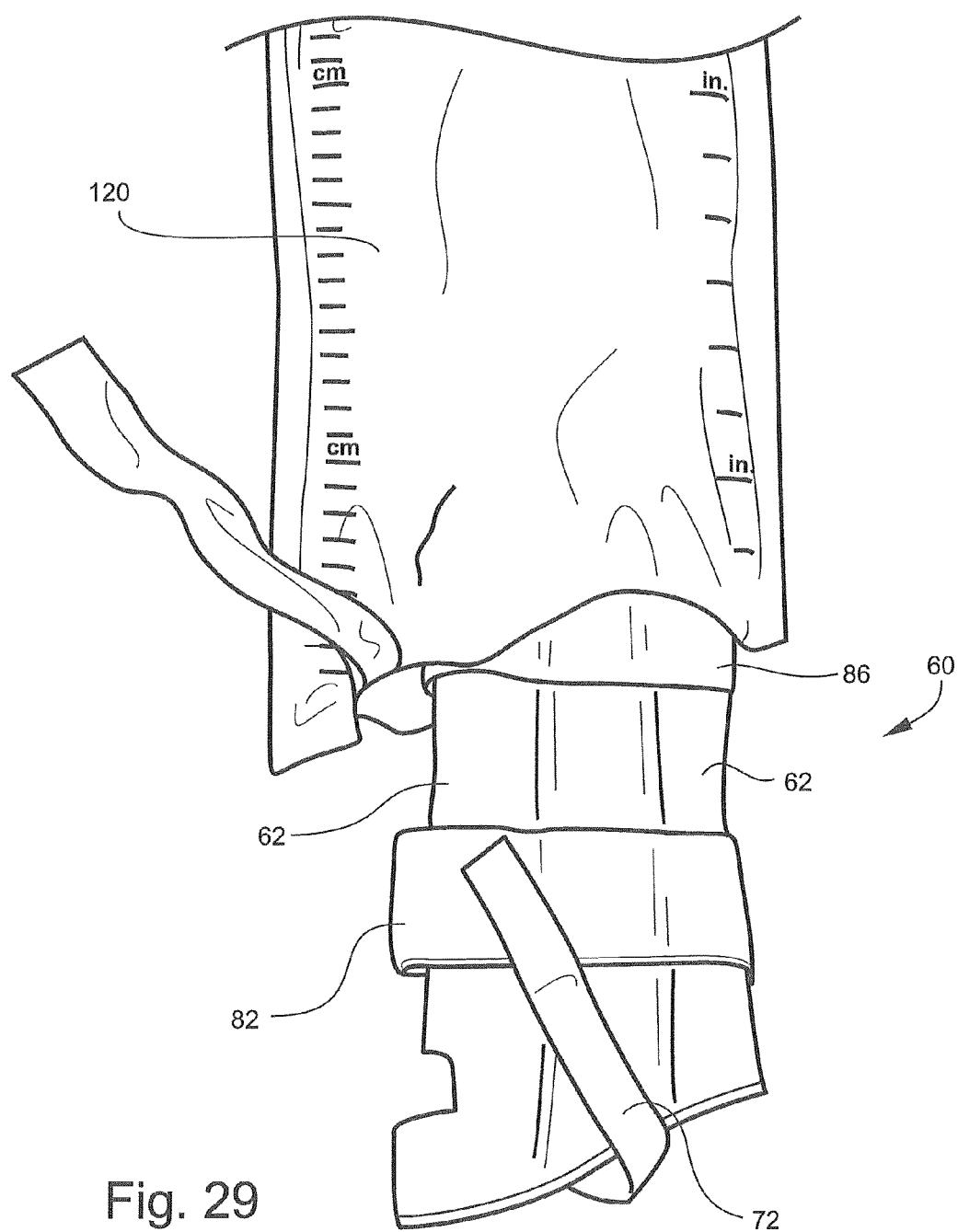
FIG. 29 illustrates the package in its opened condition with the cast positioned in the package.

Referring to FIGS. 28 and 29, the cast 30 or cast 60, cast 60 being shown, may optionally be packaged with the substrate 16 and, optionally, cover 18, prepositioned in the cast 60 and sealed in low moisture conditions in a moisture-impervious package 120. As discussed above, the substrate 16 is coated or saturated with a moisture-curable resin that hardens upon exposure to moisture. When ready to apply the cast 60, the package 120 is opened and the cast 60 is removed and wetted. The moisture readily penetrates through the fabric of the cast 60 to the substrate 16. The moistened cast 60 is placed on the limb, loosely secured together around the limb using the hook and loop elements 110, 112, and overwrapped with an elastic bandage for several minutes until the substrate 16, shaped while flexible to the limb, has hardened. Then the bandage is removed and the cast 60 is secured in place with the straps 72, 84 and 86. The same process can be carried out with the cast 30.

As shown in FIGS. 17 and 18, a roll-form type of splint material may be used as an alternative to the pre-cut substrate described above. This type of splint material is fully described in applicant's U.S. Pat. No. 4,770,299. As described above, the splint is prepared and applied to the patient as a splint during an acute phase of treatment. Thereafter, the cover surrounding the substrate is preferably removed, and the molded substrate is mated with the cast 30 or cast 60, also as described above.

Moisture resistant moldable injury therapy devices and methods are described above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. A moisture-resistant multi-phase orthopedic system, comprising:
   (a) a sleeve formed of moisture-impervious material and sealable to prevent entry of moisture;
   (b) a moldable splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb;
   (c) an elongate removable wrap for retaining the splint on the limb; and
   (d) a removable cast for application to the limb during a subsequent treatment phase, and comprising:
      (1) a cast body having an interior side and exterior side and formed of a moisture resistant, single layer, three-dimensional double knit fabric having an open structure for providing enhanced moisture transfer; and
      (2) a flap carried by the cast body and movable between an open position, and a closed position overlying a part of the cast body to be applied to a treatment area of the limb, the flap adapted to cover and retain between the cast body and the flap, the splint worn by the patient during the initial treatment phase in a same location as the splint during the initial treatment phase.

2. A moisture-resistant multi-phase orthopedic system according to claim 1, wherein the substrate is pre-formed into a shape suitable for application to the limb to be treated.

3. A moisture-resistant multi-phase orthopedic system according to claim 1, wherein the moisture resistant, single layer, three-dimensional double knit fabric has a moisture transfer rate (MVTR) of between 500 and 600 g/m$^2$/24 hrs.

4. A moisture-resistant multi-phase orthopedic system according to claim 1, wherein the moisture resistant, single layer, three-dimensional double knit fabric has a moisture transfer rate (MVTR) of about 560 g/m$^2$/24 hrs.

5. A moisture-resistant multi-phase orthopedic system according to claim 3, wherein the removable cast includes a padding layer positioned on the removable cast to overlie a part of the cast body to be applied to the treatment area of the limb.

6. A moisture-resistant multi-phase orthopedic system according to claim 3, wherein the removable cast comprises a short arm cast adapted for being placed on a forearm of the patient, and includes a thumb recess portion positioned for receiving a thumb and a retention strap for retaining the thumb recess portion around the thumb.

7. A method of immobilizing a limb in multiple treatment phases, comprising the steps of:
   (a) providing:
      (i) a sleeve formed of moisture-impervious material and sealable to prevent entry of moisture;
      (ii) a splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb;
      (iii) an elongate removable wrap for retaining the splint on the limb; and
      (iv) a removable cast for application to the limb, and comprising a cast body having an interior side and exterior side and formed of a moisture resistant, single layer, three-dimensional double knit fabric having an open structure for enhanced moisture transfer from skin of the patient outwardly; and a flap carried by the cast body and movable between an open position, and a closed position overlying a part of the cast body to be applied to a treatment area of the limb, the flap adapted to cover and retain the splint between the cast body and the flap;
   (b) removing the splint from the sleeve and wetting the splint;
   (c) molding the splint to the limb;
   (d) securing the splint in its molded position to the limb for being worn during an initial orthopedic treatment phase;
   (e) removing the splint from the limb; and
   (f) placing the splint between the flap and the cast body of the cast; and
   releasably applying the cast and the splint to the limb for being worn during a subsequent orthopedic treatment phase.

8. A method according to claim 7, wherein the moisture resistant, single layer, three-dimensional double knit fabric has a moisture transfer rate (MVTR) of between 500 and 600 g/m$^2$/24 hrs.

9. A method according to claim 7, wherein the moisture resistant, single layer, three-dimensional double knit fabric has a moisture transfer rate (MVTR) of about 560 g/m$^2$/24 hrs.

10. A method according to claim 7, and including the step of pre-forming the substrate into a shape suitable for application to the limb to be treated.

11. A method according to claim 7, and including the step of providing an elongate medical bandage material substantially a same length as the sleeve and positioned in the sleeve in a single length along the length of the sleeve, and a seal for resealing the sleeve against entry of moisture after a predetermined length of the bandage material has been dispensed from the sleeve for use to prevent hardening of the substrate of the bandage material remaining in the sleeve.

12. A method according to claim 7, and including the step of removing the cover from the substrate before placing the splint between the flap and the cast body of the cast.

13. A method according to claim 7, and including the steps of:
(a) placing the substrate with a moisture-curable resin coated thereon or impregnated therein in a moisture-impervious package;
(b) sealing the cast and substrate in the moisture-impervious package in a moisture free condition until use;
(c) when ready for use, opening the package, removing the cast and splint, wetting at least the substrate, and applying the cast and splint to the limb to be supported by the cast;
(d) forming the cast to the limb until the substrate has hardened in a desired limb-supporting condition; and
(e) securing the cast to the limb.

14. A moisture-resistant removable cast for application to a limb during an orthopedic treatment phase, and comprising:
(a) a cast body having an interior side and exterior side; and
(b) a flap carried by the cast body and formed of a moisture resistant, single layer, three-dimensional double knit fabric having an open structure for enhanced moisture transfer and movable between an open position, and a closed position overlying a part of the cast body to be applied to a treatment area of the limb, the flap adapted to cover and retain between the cast body and the flap, a splint worn by a patient during an initial treatment phase.

15. A moisture-resistant removable cast according to claim 14, and including a padding layer positioned on the cast to overlie a part of the cast body to be applied to the treatment area of the limb.

16. A moisture-resistant multi-phase orthopedic system according to claim 14, wherein the moisture resistant, single layer, three-dimensional double knit fabric has a moisture transfer rate (MVTR) of between 500 and 600 $g/m^2/24$ hrs.

17. A moisture-resistant multi-phase orthopedic system according to claim 14, wherein the moisture resistant, single layer, three-dimensional double knit fabric has a moisture transfer rate (MVTR) of about 560 $g/m^2/24$ hrs.

* * * * *